US008506502B2

(12) United States Patent
Gilhuly

(10) Patent No.: US 8,506,502 B2
(45) Date of Patent: Aug. 13, 2013

(54) SENSORS AND SENSING FOR MONITORING NEUROMUSCULAR BLOCKADE

(76) Inventor: Terence Gilhuly, Vancouver (CA)

( * ) Notice: Subject to any disclaimer, the term of this patent is extended or adjusted under 35 U.S.C. 154(b) by 720 days.

(21) Appl. No.: 12/311,105

(22) PCT Filed: Sep. 14, 2007

(86) PCT No.: PCT/CA2007/001606
§ 371 (c)(1),
(2), (4) Date: Mar. 19, 2009

(87) PCT Pub. No.: WO2008/031209
PCT Pub. Date: Mar. 20, 2008

(65) Prior Publication Data
US 2010/0081963 A1 Apr. 1, 2010

Related U.S. Application Data

(60) Provisional application No. 60/825,903, filed on Sep. 16, 2006, provisional application No. 60/825,904, filed on Sep. 16, 2006.

(51) Int. Cl.
A61B 5/05 (2006.01)
(52) U.S. Cl.
USPC ............................................ 600/554; 604/31
(58) Field of Classification Search
USPC .......................................... 600/554; 604/31
See application file for complete search history.

(56) References Cited

U.S. PATENT DOCUMENTS

| 3,590,810 | A |   | 7/1971 | Kopecky |
|---|---|---|---|---|
| 4,144,893 | A |   | 3/1979 | Hickey |
| 4,291,705 | A |   | 9/1981 | Severinghaus |
| 4,387,723 | A | * | 6/1983 | Atlee et al. .................... 600/554 |
| 4,595,018 | A |   | 6/1986 | Rantala |
| 4,817,628 | A |   | 4/1989 | Zealear |
| 4,848,359 | A |   | 7/1989 | Bournonville |
| 5,131,401 | A |   | 7/1992 | Westenskow |
| 5,391,081 | A |   | 2/1995 | Lampotang |
| 5,626,622 | A |   | 5/1997 | Cooper |
| 5,813,404 | A |   | 9/1998 | Devlin |
| 5,957,860 | A |   | 9/1999 | Rodiera Olive |

(Continued)

FOREIGN PATENT DOCUMENTS

WO WO 2006/015938 2/2006

OTHER PUBLICATIONS

D.A. Linkens et al, "Identification and control of muscle-relaxant anaesthesia", IEE Proceedings-D, 1982, pp. 136-141, 129(4), IEE, United Kingdom.

(Continued)

Primary Examiner — Brian Szmal
Assistant Examiner — Emily Lloyd

(57) ABSTRACT

Improved sensors and sensing methods for detection of Neuromuscular Blockade (NMB), for example to improve monitoring generally, as well as facilitate automated NMB drug administration. The methods, systems, devices, etc., herein can increase the quantity and quality of data available. The methods, etc., include translation between commonly available sensing types, use of partially saturated sensor measurements, use of a model of neurotransmitter storage and release and sophisticated use of more than one sensor simultaneously. These methods are aided by new sensors and methods of decreasing electrical noise. An implementation of the methods, systems, devices, etc., herein is automated drug delivery for NMB, whether through an advisor system or through with full computer control.

24 Claims, 10 Drawing Sheets

(56) References Cited

U.S. PATENT DOCUMENTS

| | | | |
|---|---|---|---|
| 6,032,064 | A | 2/2000 | Devlin |
| 6,236,874 | B1 | 5/2001 | Devlin |
| 6,389,312 | B1* | 5/2002 | Duckett ............ 600/546 |
| 6,625,481 | B2 | 9/2003 | Bennett |
| 6,725,086 | B2 | 4/2004 | Marinello |
| 2003/0165261 | A1* | 9/2003 | Johansen et al. ............ 382/124 |
| 2003/0195587 | A1 | 10/2003 | Rigaux et al. |
| 2008/0012578 | A1 | 1/2008 | Campbell |

OTHER PUBLICATIONS

R. Miller, "Pharmacokinetics of Muscle Relaxants and their Antagonists", Pharmacokinetics of Anaesthesia, 1984, chapter 11, Blackwell Scientific Publications, United Kingdom.

T. Gilhuly et al, "Modeling for Computer Controlled Neuromuscular Blockade", Proceedings of the 27th Annual International Conference of the IEEE Engineeiing in Medicine and Biology Society, 2005, TBD pages, IEEE, United States.

A.D. MaCleod et al, "Automatic control of neuromuscular block with atracurium", British Journal of Anaesthesia, 1985, pp. 31-35, vol. 63, United Kingdom.

C.M. Wait et al, "Feedback control of neuromuscular blockade: A simple system for infusion of atracurium", Anaesthesia, 1987, pp. 1212-1217, vol. 42, United Kingdom.

B.H. Brown et al, "Closed-loop control of muscle relaxation during surgery", Clinical Physics and Physiological Measurement, 1980, pp. 203-210, vol. 1, United Kingdom.

D.A. Linkens et al, "Smith predictor and self-tuning control of muscle-relaxant drug administration", IEE Proceedings-D, 1985, pp. 212-216, vol. 132(5), United Kingdom.

D.G. Mason et al, "Self-Learning Fuzzy Control with Temporal Knowledge for Atracurium-Induced Neuromuscular Block during Surgery", Computers and Biomedical Research, 1999, pp. 187-197, vol. 32, United Kingdom.

H.H. Ali et al, "Quantitative assesment of residual antidepolarizing bloack (part I)", British Journal of Anaesthesia, 1971, pp. 473-477, vol. 43, United Kingdom.

P.M. Schumacher et al, "Model-based control of neuromuscular block using mivacurium: design and clinical verification", European Journal of Anaesthesiology, 2006, pp. 691-699, vol. 23, United Kingdom.

N.R. Webster et al, "Closed-loop administration of atracurium", Anaesthesia, 1987, pp. 1085-1091, vol. 42, United Kingdom.

T. Mendonca et al, "PID control strategies for the automatic control of neuromuscular blockade", Control Engineering Practice, 1998, pp. 1225-1231, vol. 6, United States.

K.J. Astrom, "Adaptive Feedback Control", Proceedings of the IEEE, 1987, pp. 185-217, vol. 75(2), IEEE, United States.

D.W. Clarke et al, "Generalized Predictive Control—Part I. The Basic Algorithm", Automatica, 1987, pp. 137-148, vol. 23, United Kingdom.

D.W. Clarke et al, "Generalized Predictive Control—Part II. Extensions and Interpretations", Automatica, 1987, pp. 149-160, 1987, Untied Kingdom.

M. Mahfouf et al, "Generalized predictive control (GPC) in the operating theatre", IEE Proceedings-D, 1992, pp. 404-420, vol. 139(4), United Kingdom.

C.M. Lee, "Train-of-4 Quantitation of Competitive Neuromuscular Block", Anesthesia and Analgesia, 1975, pp. 649-653, vol. 54(5), United States.

J. Engbaek et al, "Double burst stimulation (DBS): a new pattern of nerve stimulation to identify reisual neuromuscular block", British Journal of Anaesthesia, 1989, pp. 274-278, vol. 62, United Kingdom.

H. Kirkegård-Nielsen et al. "Response to double burst appears before response to train-of-four stimulation during recovery from non-depolarizing neuromuscular blockade", Acta Anaesthesiologica Scandinavica, 1996, pp. 719-723, Sweden.

H.H. Ali et al, "Monitoring of Neuromuscular Function", Anesthesiology, 1976, 216-249, vol. 45(2), Untied States.

T.A. Torda, "Monitoring neuromuscular trnasmission", Anaesthesia Intensive Care, 2002, pp. 123-133, vol. 30, United States.

Organon Incorporated, "Zemuron (Rocuronium Bromide) Injection Investigator's Brochure", 2000, Akzo-Nobel, West Orange, NJ, United States.

W.D.M. Paton et al, "The margin of safety of neuromuscular transmission", Journal of Physiology, 1967, pp. 59-90, vol. 191, United States.

D.M.J. Quastel et al, "Receptor Blockade and Synaptic function", Journal of Neural Transmission, 1983, pp. 61-81, vol. 18 Supplemental, United States.

P. Pennafather et al, "Relation between synaptic receptor blockade and response to quantal transmitter at the mouse neuromuscular junction", Journal of General Physiology, 1981, pp. 314-344, vol. 78, United States.

T. Egan et al, "Target-controlled Infusions for Intravenous Anesthetics; Surfing USA Not!", Anesthesiology, 2003, pp. 1039-1041, vol. 99, United States.

P. Schultz et al, "Onset and duration of action of rocuronium—from tracheal intubation, through complete block to recovery", Acta Anaesthesia Scandinavia, 2001, pp. 612-617, vol. 45, Sweden.

H.K. Nielsen et al, "Double burst stimulation for monitoring profound neuromuscular blockade: a comparison with posttetanic count and train-of-four", Acta Anaesthesiologica Belgica, 1992, pp. 243-257, vol. 43(4), Belgium.

H.H. Ali et al. "Stimulus Frequency in the detection of neuromuscular block in humans", British Journal of Anesthesiology, 1970, pp. 967-978, vol. 42, United Kingdom.

D. Elmqvist et al, "A quantitative study of end-plate potentials in isolated human muscle", Journal of Physiology, 1965, 505-529, vol. 178, United Kingdom.

* cited by examiner

SENSORS AND SENSING FOR MONITORING NEUROMUSCULAR BLOCKADE

CROSS-REFERENCE TO RELATED APPLICATIONS

The present application claims priority from United States provisional patent application No. Ser. No. 60/825,903, filed Sep. 16, 2006, and from U.S. provisional patent application No. 60/825,904, filed Sep. 16, 2006, and pursued as PCT applications PCT/CA2007/001605 and PCT/CA2008/001606.

BACKGROUND

Automated drug delivery (or drug administration under computer guidance or control) can improve drug therapy by allowing for more efficient and smoother delivery. This may reduce drug usage, side effects and costs; permit health care staff to work more efficiently; and allow the safe use of drugs that are difficult to administer manually, leading to better care for the patient. One example is automatic drug delivery, with the development of models and control methods specifically for control of neuromuscular blockade (NMB). NMB drugs produce paralysis to prevent motion, for example to permit tracheal intubation and allow access to deep structures with smaller incisions.

As NMB drugs have high therapeutic indices in hospital settings, they are often used in excess of minimal effective requirements. A strategy for administration is to provide an overdose to prolong paralysis, monitor for returning muscle function and, once it returns, overdose again [1]. The large dose delivers rapid onset of paralysis, quicker surgical conditions, and avoids titration to a precise anesthetic setpoint and regulation once there [2].

Unfortunately this approach can reduce fine control and can increase toxicity. Fine control can be preferable during surgeries where knowledge of the patient's state is important for safety. For example, in Harrington rod insertion for reshaping the spine, the surgeon assesses whether or not the rods have impinged nerves by the ability of the patient to respond physically. Testing can be performed only after the return of muscle function. Under automatic control the patient minimally can be kept minimally paralyzed until a test is required, reduce drug administration to allow function to return, and then re-paralyze for continued work with minimal waiting time by the surgical staff.

The overdosing strategy is also a source of inconvenience if complications arise and the surgical conditions change, which is not uncommon. An example of this was seen in the study used to collect data for the NMB Advisory System (NMBAS) initial patient model [3]. After paralysis and induction of anesthesia had taken place, examination of the patient revealed extensive invasive carcinoma. The procedure was cancelled, and the anesthesiologist and attending nurses monitored the patient until the drug wore off enough that the patient could be reversed.

Computer control of NMB has been attempted previously. Researchers have been able to deliver blockade at a near-constant controlled, setable level compared to conventional practice, while using less drug [1, 4]. Representative efforts include bang-bang [5], Proportional Integral Derivative (PID) control [6], and PID/Smith predictor [7] and fuzzy logic control [8]. Some of the controllers developed have not been stable or robust enough to handle the intra- and interpatient variability present.

Other controllers have achieved near constant levels of blockade in relatively controlled experimental settings, but are associated with significant constraints that thus far have impeded their utility in routine clinical practice. For example, most involve the use of single twitch stimulation to measure response (ST or T1%). In addition to the often considerable associated setup time, the use of single twitch stimulation necessitates a stable control [9] and T1% baseline stabilization requires up to 20 minutes between induction and NMB drug administration [10], unnecessarily exposing patients to the risks of an unprotected airway and creating unacceptable operating room time delays. Furthermore, the typical controller setpoint was T1%=10% (i.e., 90% single twitch suppression) [8, 10, 11, 12] which represents a potentially non-reversible state.

Adaptive control techniques may help accommodate the patient variance. An adaptive controller is a fixed structure controller with adjustable parameters and a mechanism for automatically adjusting those parameters. Adaptive control's roots begin in the 1950s with the development of the autopilot for high-performance aircraft [13]. Since then there has been much theoretical development and application. An in-depth review of this field appears in [13].

An example of an adaptive control technique that has been used not just in chemical batch processes but in clinical application as well is Generalized Predictive Control [14, 15], a general-purpose adaptive control method. This method was used in the operating room in control of NMB as described in [16].

BRIEF SUMMARY

Presented here are methods and devices for aiding automated NMB delivery by better using data that is available with commonly available sensing modalities, by increasing the amount of data available, and by improving on the existing devices to aid user acceptance.

Computer control of drug therapies is difficult for various reasons (see [27]), but one of the greatest reasons is an inability to trust automated systems due to their failure to produce accurate and smooth levels of response over a broad spectrum of patients. One reason for the lack of accurate and smooth levels is an inability to manage patient variance, which may be because of and largely due to the lack of reliable data available to the control algorithms—a problem that occurs with measurement of neuromuscular function.

Furthermore, automating drug administration typically needs large amounts of data by the pharmacokinetic models for appropriate modeling of the patient. Patients are highly variable, having vast differences in age, sex, race, height, weight, BMI, organ pathology and many other parameters influencing drug absorption, distribution, metabolism and excretion. Model based controllers thus need lots of data to represent individual patients. Non-model based control schemes generally are not used, as they typically cannot manage parameter variation beyond 30% of initial estimates. Furthermore, patients can change during their procedure pharmacologically, with tolerance and sensitization directly affecting response; and blood volume, pH and temperature changes, and drug interactions doing so indirectly.

This problem is exacerbated in control of NMB drugs as data is typically scarce. Limits on how frequently muscles can be stimulated reduce the quantity of data. Sensing should not be done continuously as the sensing methods can affect the measurement by reducing the replaceable but finite supplies of neuromuscular transmitter, acetylcholine (ACh). As stated above, the best measurement under most circumstances is the TOF, and this is typically used only once every twenty seconds. In addition, due to the limited range of detection of current sensing methods quality of data is reduced.

In one aspect, use is made of available data by modification and reinterpretation of commonly used sensing techniques. In one instantiation, the information on when twitches disappear with increased levels of NMB is used to construct linear, sigmoidal and other T1 to TOF conversion relationships that can ascribe value in terms of TOF measurements to TOF measurements with less than four twitches. In another instantiation, the amount of available data is increased by converting measurements between stimulation modes.

In a second aspect, data available is increased. In one instantiation of this aspect, new measures of NMB based on incomplete TOF measurements are constructed. Ratios of the third to the first (To3) and the second to the first twitches (To2) are converted to corresponding TOF values to make the data more continuous. In another instantiation, flow of the neuromuscular junction (NMJ) neurotransmitter acetylcholine (ACh) is modeled. This model is used to predict response, plan stimulation to produce maximum information on the patient state, and classify the patient. This ACh inventory model can also be used to find the minimal amount of time needed between standard stimuli type, and to facilitate and plan overstimulation to gather more data at key junctures and to allow classification or other judgments to be made with equal amounts of data and therefore with equal likelihood of success as for the usual stimulation schedule, but in less time.

In a third aspect, data available is increased with a sensor comprising one or more stimulator and multiple sensing devices. In one instantiation, multiple sensors are situated on different muscles to use muscles with different sensitivity to NMB drugs to expand the (unsaturated) range of sensing and control. In another instantiation, multiple sensors are situated on similar muscles to allow reduction of time between stimuli by alternating stimulation between the two groups to reduce the average period of stimulation. In another instantiation, multiple sensors are situated on similar muscles for overstimulation to get more data and then switch when one is "tired" or upregulated. In another instantiation, multiple sensors are situated on pairs of multiple groups to allow reduction of time between stimuli and to take advantage of different sensitivities between the groups. In another instantiation, multiple sensors are situated on similar muscle groups to allow overstimulation of one of the muscles to learn of ACh production and inventory capabilities while control is done with the other at regular stimulation rates. In another instantiation, multiple sensors are situated on a combination of different and similar muscles with sensing at fast and slow twitch muscle types to extend the sensing range, and use of exhaustion and/or reduction of the sampling period to increase the available data.

In a fourth aspect, NMT stimulation monitors comprise decreasing setup times, reducing complexity and increasing accuracy and standardizing electrode placement to reduce error. One instantiation embeds the stimulation electrodes and sensing elements into a patient wearable glove, to permit quick and accurate placing of electrodes. Another instantiation embeds the electrodes and sensing element into a bandage. In a fifth aspect, a novel shielding apparatus for the sensor is used to increase data quantity by reducing corruption of data due to cautery and other electrical noise.

One embodiment is comprised of one or more sensors for detecting the level of neuromuscular blockade (the sensor), a device for processing the sensor data and operating the algorithms presented herein (the computation unit), a display to present the measured and calculated data to the anesthesiologist and other medical staff (the user), and methods of obtaining input from the user and anesthesia monitor. The sensor can comprise any NMB response transducer (e.g. electromyographic, force, strain or other) temporarily fixed to the patient, with appropriate data conversion (analog to digital conversion) to make the data usable by the computational unit. Optionally this can be a multiple sensor system with more than one sensor temporarily attached to similar or different muscles. The sensor is optionally in the form of the sensors described herein. The sensor can be used with or without shielding, either shielded wires or the conductive shielding bag or hood described herein. The devices for monitoring can be contained in a module for insertion permanently or temporarily into the anesthetic monitor, as is done with some neurostimulator modules. The containment can also be in the form of a standalone unit positioned in association with the patient and/or the monitor. The algorithms can comprise one or more of the following: a method of interpreting partial TOF measurements in terms of TOF measurements; a method of interpreting PTC measurements in terms of TOF measurements when the patient is too paralyzed to produce response with the TOF; a method or methods of interpreting other measurement modalities as TOF measurements; a method of increased data collection through measurement of response in more than one muscle; and a method of estimating the amount of available neurotransmitter for determining appropriate stimuli, for validating response, for translating overstimulation to normal conditions and for support of data gathered at higher rates than recommended. If multiple sensors are used, methods of using them can comprise: alternate use of the sensors to take advantage of different responses in muscle groups, and alternate use of the sensors to effectively stimulate at a higher frequency than normally possible. A multiple sensor system can have appropriate algorithms for co-ordination and control of stimuli at the different sensors and for interpreting measurements made.

DETAILED DESCRIPTION

Figure 1:
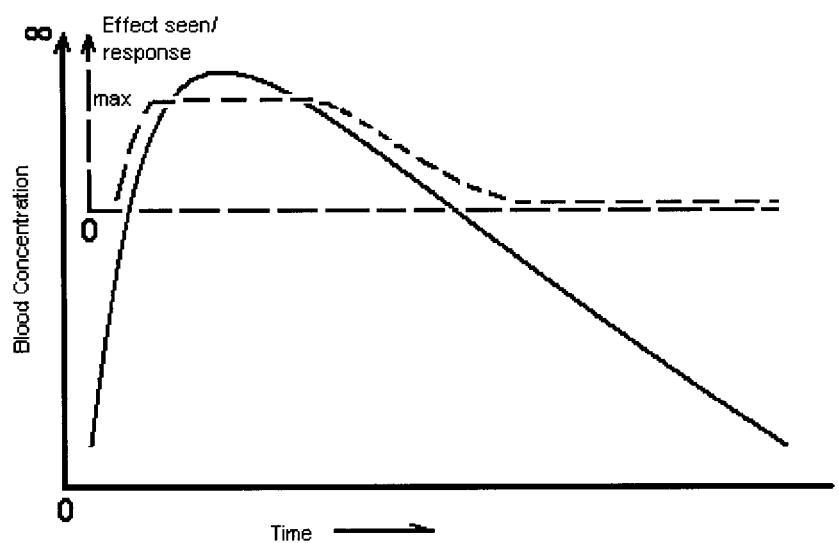
FIG. 1 illustrates a relationship between blood concentration of a drug and response over time.

In this section, exemplary mathematical fits and correlations of data are presented. Fits of the data are specific for the purpose of providing an example. Other data and/or other methods of fitting (e.g. polynomial, exponential, linear or other) can produce fits that may be different but adequate and in the spirit of methods, systems, devices, etc., herein.

Neuromuscular Monitoring Techniques

Neuromuscular stimulating techniques available to the anesthesiologist via the commercially produced stimulators can include train-of-four (TOF), single twitch (ST), double burst (DBS) and post-tetanic count (PTC).

The most commonly used neuromuscular sensing modality is the train-of-four measurement (TOF) by electrostimulation. The train-of-four (TOF) typically uses four brief (between 100 and 300 µs) current pulses (generally less than 70 mA) at 2 Hz, repeated every 10 to 20 s as electrostimulation. The resulting twitches are measured and quantified for electromyographic response, force, acceleration, deflection or another means. The first—the T1 twitch, and the last—the T4 twitch, are compared, and the ratio of the two gives an estimate of the level of NMB. Stimuli series are spaced by ten or more seconds (generally 20 s is used to provide a margin of safety) to give a rest period for full restoration of steady state conditions—faster stimulation results in smaller evoked responses [17].

The ST measurement is a single electrical pulse of between 100 and 300 µs, repeated at intervals greater than or equal to one second. Typically, four seconds are needed between stimuli to prevent upregulation and alteration of the true muscle response. An ST measurement taken when the stimulation regime is first started is recorded as the control, labeled T0. The ST measurement is a ratio of the latest measured muscle twitch compared to the T0 value.

Double burst stimulation (DBS) can comprise two bursts of two to four stimulations given at high frequency and separated by a brief intermission. If the stimulation frequency is greater than 40 Hz and the interval between the bursts is not too short then two separate contractions will occur. Two groups of stimuli of three pulses each at 50 Hz, spaced by 750 ms, and all repeated once every 10 s was judged the most appropriate [18]. DBS is quantified by taking the ratio of the height of the second pulse relative to the first. The DBS was initially proposed for monitoring profound block more frequently than can be done with PTC [19].

PTC can be used in deep blockade as a means of evoking a large ACh output in order to over-whelm temporarily the NMB. It is a five second long 50 Hz stimulation followed by a three second resting period and then up to thirty ST impulses at one per second. The number of impulses that can be measured indicates the degree of blockade.

Comparing many commonly available stimulation methods, TOF can be typically less sensitive than tetanus, but more sensitive than double burst stimulation (DBS) and single twitch stimulation (ST). Tetanus can be very uncomfortable and can typically be repeated only once every five or more minutes to avoid influencing the measurement. TOF can be advantageous because as a ratio of concurrent pulse it does not require a pre-recorded control value for comparison, and it has immunity to changing baseline measurements [20] unlike the ST. TOF can be the recommended stimulus for use in onset, normal block, judging reversibility and recovery conditions. However, due to lack of response, TOF can be not used for deep blockade. DBS can be comparable in recovery to TOF and has some use in deep block. DBS can also be used in normal block and judging reversibility, but TOF can be superior. Tetanus has some use in onset, normal block and deep block conditions. Post-tetanic count (PTC) and post-tetanic burst (PTB) are best at, and should only be used for, deep block conditions [21] due to their painful nature.

Stimulation of Different Muscles

The qualities that can make a muscle appropriate for assessing response are accessibility, and ability to represent the diaphragm and other muscles of breathing. The muscles of the hand and face are used most commonly. These groups are typically highly accessible (although they can be covered by drapes) and easy to apply monitoring equipment to. Muscles of the lower legs can be impractical as the large motions they create can be distracting, obstructive and dangerous. The face is convenient to access but the specific muscles are difficult to stimulate individually.

Different muscles are different anatomically and because of this muscles can respond differently to NMB drugs. The adductor pollicis and corrugator supercilii are typically on opposite ends of the response spectrum, with corrugator supercilii being one of the most resistant to NMB drugs and adductor pollicis being one of the most sensitive. Suitability of muscles for neuromuscular monitoring has been studied and results summarized in [21]. Adductor pollicis and abductor digitorum minimi were found to be best for reversability and recovery, good for normal block and only slightly useful for onset. Gastrocnemius was found to be only slightly useful for onset, deep block and normal block; and good for reversability and recovery. Flexor hallucis brevis was found to be similar to the gastrocnemius but was slightly better for monitoring normal block. Corrugator supercilii was found to be best for onset, deep and normal block; was good for reversibility; and mediocre for recovery.

The Patient Model

For this system, the patient drug induced response is represented by a Laguerre model. Other model structures can be used as well.

A Laguerre model is an orthonormal series representation of a plant's dynamics. Laguerre models are used for their convenient network realization, transient signal similarity (important for responsive process control), and similarity to Pade approximation useful for identifying time delays. This model has a simple representation and flexible structure, allowing for easy adaptation [22]. A Laguerre model is defined by the state space representation:

$$L(k+1)=AL(k)+Bu(k)$$

$$y(k)=CL(k) \quad (1)$$

where u is the input—the amount of drug given in multiples of a standardized dose (e.g. 2×ED 95), y is the output, k is the timestep and L is the patient state vector representing flow of input (drug) through the patient, A and B are the state space matrix and input gain vector, and C is the Laguerre model coeffcient vector, a vector of gains to weight the components of the state vector defined by a least squares estimation on these equations. A and B are dimensioned by the number of filters and defined by the Laguerre filter pole p as:

$$A(i,j) = \begin{cases} p \\ (1-p^2)(-p)^{i-j-1} \\ 0, \end{cases} \quad (2)$$

$$\text{if } \begin{cases} i = j \\ i > j \\ \text{otherwise} \end{cases}$$

$$B(i) = \sqrt{1-p^2}\,(-p)^{i-1}$$

The Laguerre filter pole can be optimized for each patient model by a linear search algorithm to provide a best fit of the impulse response data. C vector parameters are typically individual to each patient, and can be found through a nonlinear estimation of impulse response data. For the NMB studies related to this work, impulse responses were found using doses 0.6 mg/kg rocuronium, as this is the manufacturer's recommended intubation dose. This dose is equal to the 2×ED 95 dose (double the dose that is effective for 95% of the population) [23]. The response modeled was the measurement from the neuromuscular monitoring sensor (accelerometry, mechanomyography and electromyography are common transduction methods), converted into pseudo-occupancy, a linearized assessment of receptor occupancy by the blocking drug, to be explained later.

Models of response to pharmaceuticals can be composed of two parts. The first part typically is a description of the drug flow through the subject and is generally a linear differential equation of the form:

$$c(t) = \sum_{i=1}^{N} a_i e^{-\lambda_i t} \qquad (3)$$

where c(t) is the concentration of the drug, $a_i$ is a gain and $\lambda_i$ is the disposition constant for the $i^{th}$ compartment, and N is the order of the compartmental model used to model the drug. The second stage typically incorporates the nonlinearities in the relationship between drug administration and response. When drugs are administered, measurements can experience nonlinearities in the form of delay to action and saturation of response. These nonlinearities are related to the pharmacological terms of potency and efficacy. Delay exists because it may be necessary to agonize (antagonize for blocking drugs) a proportion of receptors before response is seen. The apparently non-operational proportion is known as the "receptor reserve". Saturation occurs because the maximum response has been met either by agonizing all the receptors or a large enough percentage of the receptors to achieve that response. Mathematically, these nonlinearities can be seen at low and high concentrations when effect as a function of drug concentration is defined by the sigmoidally shaped Hill equation:

$$E(c) = E_{max} \frac{c^\gamma}{c^\gamma + EC_{50}^\gamma} \qquad (4)$$

where E is effect, $E_{max}$ is the maximum effect possible, c is the concentration of the agent at the NMJ, γ is the Hill coeffcient corresponding to the slope of the curve, and $EC_{50}$ is the effective concentration producing a 50% response.

These nonlinearities can be seen in FIG. 1. As drug is added to the patient, it distributes throughout and the concentration at the region of interest rises. At first effect is zero. After the drug has enjoined enough receptors, a threshold is typically reached and the effect starts to be seen. Effect increases with concentration to the point of saturation of the response (and/or sensor) after which effect plateaus. Concentration can continue to rise but there is no increase in effect. Considering only the primary action of the drug and neglecting side effects, concentrations above this level produce no greater effect but instead just extend the amount of time in saturation. Function returns with elimination of the excess drug.

An example of a system with receptor reserve is the neuromuscular junction (NMJ). The NMJ, where NMB drugs act, typically has reserve receptors to increase probability of contraction on stimulation and decrease likelihood of blockade. The NMJ also has a saturation level as an infinite amount of force cannot be generated, and with regards to administration of NMB drugs, after a certain percentage of the receptors are blocked no contraction can be had. In [24], isolated cat anterior tibialis and sartorius muscles were stimulated in the presence of tubocurarine and other NMB drugs at known concentrations. It was estimated that 76% of the receptors had to be blocked by the antagonist before block was noticeable, and 92% of the receptors had to be blocked for near complete blockade. Results for receptor reserve were obtained for humans in [25, 26]. To quantify the proportion of receptors necessary to be blocked to diminish single twitch (similar to the T1 response) stimulation, end plate potentials at human intercostal muscle NMJs were measured. Reduction in response for the single twitch started at approximately 60% blockade with a 50% decay occurring at approximately 80% occupancy.

PATENT DOCUMENTS

See U.S. Pat. Nos. 3,590,810, 4,144,893, 4,291,705, 4,387,723, 4,387,723, 4,595,018, 4,817,628, 4,848,359, 5,131,401, 5,391,081, 5,626,622, 5,813,404, 5,957,860, 6,032,064, 6,236,874, 6,389,312, 6,625,481 and 6,725,086; and US applications 2003/0195587 and 2008/0012578; and WIPO 2006/015938.

REFERENCES

[1] D. A. Linkens, A. J. Asbury, S. J. Rimmer, and M. Menad. Identification and control of muscle-relaxant anaesthesia. IEE Proceedings-D, 129(4):136-141, 1982.

[2] R. Miller. "Pharmacokinetics of Muscle Relaxants and their Antagonists", chapter 11 of Pharmacokinetics of Anaesthesia. Blackwell Scientific Publications, 1984.

[3] T. Gilhuly, G. Dumont, and B. MacLeod. Modeling for Computer Controlled Neuromuscular Blockade. In Proceedings of the 27 th Annual International Conference of the IEEE Engineering in Medicine and Biology Society, Shanghai, China, September 2005.

[4] A. D. MacLeod, A. J. Asbury, W. M. Gray, and D. A. Linkens. Automatic control of neuromuscular block with atracurium. British Journal of Anaesthesia, 63:31-35, 1989.

[5] C. M. Wait, V. A. Goat, and C. E. Blogg. Feedback control of neuromuscular blockade: A simple system for infusion of atracurium. Anaesthesia, 42:1212-1217, 1987.

[6] B. H. Brown, J. Asbury, D. A. Linkens, R. Perks, and M. Anthony. Closed-loop control of muscle relaxation during surgery. Clinical Physics and Physiological Measurement, 1:203-210, 1980.

[7] D. A. Linkens, M. Menad, and A. J. Asbury. Smith predictor and self-tuning control of muscle-relaxant drug administration. IEE Proceedings-D, 132(5):212-218, 1985.

[8] D. G. Mason, J. J. Ross, N. D. Edwards, D. A. Linkens, and C. S. Reilly. Self-Learning Fuzzy Control with Temporal Knowledge for Atracurium-Induced Neuromuscular Block during Surgery. Computers and Biomedical Research, 32:187-197, 1999.

[9] H. H. Ali, J. E. Utting, and T. C. Gray. Quantitative assessment of residual antidepolarizing block (part I). British Journal of Anaesthesia, 43:473-477, 1971.

[10] P. M. Schumacher, K. S. Stadler, R. Wirz, D. Leibundgut, C. A. Pfister, and A. M. Zbinden. Model-based control of neuromuscular block using mivacurium: design and clinical verification. European Journal of Anaesthesiology, 23:691-699, 2006.

[11] N. R. Webster and A. T. Cohen. Closed-loop administration of atracurium. Anaesthesia, 42:1085-1091, 1987.

[12] T. Mendonca et al. PID control Strategies for the automatic control of neuromuscular blockade. Control Engineering Practice, 6:1225-1231, 1998.

[13] K. J. Astrom. Adaptive Feedback Control. Proceedings of the IEEE, 75(2):185-217, 1987.

[14] D. W. Clarke, C. Mohtadi, and P. S. Tuffs. Generalized Predictive Control—Part I. The Basic Algorithm. Automatica, 23:137-148, 1987.

[15] D. W. Clarke, C. Mohtadi, and P. S. Tuffs. Generalized Predictive Control—Part II. Extensions and Interpretations. Automatica, 23:149-160, 1987.

[16] M. Mahfouf, D. A. Linkens, A. J. Asbury, W. M. Gray, and J. E. Peacock. Generalized predictive control (GPC) in the operating theatre. IEE Proceedings-D, 139(4):404-420, 1992.

[17] C. M. Lee. Train-of-4 Quantitation of Competitive Neuromuscular Block. Anesthesia and Analgesia, 54(5):649-653, 1975.

[18] J. Engbaek, D. Ostergaard, and J. Viby-Mogensen. Double burst stimulation (DBS): a new pattern of nerve stimulation to identify residual neuromuscular block. British Journal of Anaesthesia, 62:274-278, 1989.

[19] H. Kirkegaard-Nielsen et al. Response to double burst appears before response to train-of-four stimulation during recovery from non-depolarizing neuromuscular blockade. Acta Anaesthesiologica Scandinavica, pages 719-723, 1996.

[20] H. H. Ali and J. J. Savarese. Monitoring of Neuromuscular Function. Anesthesiology, 45(2):216-249, 1976.

[21] T. A. Torda. Monitoring neuromuscular transmission. Anaesthesia Intensive Care, 30:123-133, 2002.

[22] C. C. Zervos. Adaptive Control Based on Orthonormal Series Representation. PhD thesis, University of British Columbia, 1988.

[23] OrganonIncorporated. Zemuron (Rocuronium Bromide) Injection Investigator's Brochure. Akzo-Nobel, West Orange, N.J., 2000.

[24] W. D. M. Paton and D. R. Waud. The margin of safety of neuromuscular transmission. Journal of Physiology, 191:59-90, 1967.

[25] D. M. J. Quastel and P. Pennefather. Receptor Blockade and Synaptic function. Journal of Neural Transmission, Supplemental 18:61-81, 1983

[26] P. Pennefather and D. M. G. Quastel. Relation between synaptic receptor blockade and response to quantal transmitter at the mouse neuromuscular junction. Journal of General Physiology, 78:314-344, 1981

[27] T. Egan and S. L. Shafer. Target-controlled Infusions for Intravenous Anesthetics: Surfing USA Not! Anesthesiology, 99:1039-41, 2003.

[28] P. Schultz et al. Onset and duration of action of rocuronium—from tracheal intubation, through complete block to recovery. Acta Anaesthesia Scandinavia, 45:612-617, 2001.

[29] H. K. Nielsen and O. May. Double burst stimulation for monitoring profound neuromuscular blockade: a comparison with posttetanic count and train-of-four. Acta Anaesthesiologica Belgica, 43(4):243-257, 1992.

[30] H. H. Ali et al. Stimulus frequency in the detection of neuromuscular block in humans. British Journal of Anesthesiology, 42:967-978, 1970.

[31] D. Elmqvist and D. M. J. Quastel. A quantitative study of end-plate potentials in isolated human muscle. Journal of Physiology, 178:505-529, 1965.

Methods to Better Use Available Data by Modifying Currently Available Techniques The Enhanced-TOF As the concentration of NMBA increases at the NMJ, the ability for the muscle to function is typically decreased and the sensor measuring this reports as such. For the TOF, muscle function will proceed to the point where the fourth twitch (the twitches decay in order from fourth to first) is no longer distinguishable from the background noise, and thus the sensor will typically report an error message or a measurement of zero. A measurement of zero indicates that the fourth twitch is unreadable, yet the first, second and third twitches may still be viable. The number of twitches remaining can be used to see into the level of muscle function beyond the saturation level of the TOF sensor and aid in modeling response and control.

A linear relationship can be made between the unsaturated TOF and accompanying T1 (the first twitch of the TOF) measurements based on the results of [17] show that the fourth, third, second and first twitch disappear once the ratio of T1 to its value in a control period (T0), has reached 25, 20, 10 and 0%. A linear fit of this data can reveal the relationship:

$$TOF = 1.2 \frac{T1}{T0} - 31\% \qquad (5)$$

The relationship can be extrapolated into the saturated TOF region by calculating TOF values at three, two, one and zero twitch counts (T1/T0 equal to 25, 20, 10 and 0%) revealing the respective TOF estimates −0.7, −6.8, −19 and −31%. This is in Table 1. TOF measurements in which partial twitch counts are used will be called enhanced-TOF or eTOF measurements in this work.

TABLE 1

T1/T0 vs. TOF measurements, reported + in [17] and extrapolations based on a linear relationship between T1/T0 and TOF.

| # of Twitches | 4 | 4 | 3 | 2 | 1 | 0 |
|---|---|---|---|---|---|---|
| T1/T0 [%][†] | 100 | 95 | 25 | 20 | 10 | 0 |
| TOF [%][†] | 100 | 75 | 0 | 0 | 0 | 0 |
| TOF [%]extrapolated | 91 | 85 | −0.7 | −6.8 | −19 | −31 |

Negative values of TOF are sometimes not intuitive. To make this process more understandable and to provide an approximation of receptor occupancy and blood concentration levels of NMBA for the user's (in regular practice) and computer's (for modeling and control) uses, the negative values of TOF can be converted to a positive, relaxation measure. Relaxation herein is defined as a fractional measure of paralysis ranging from 0 to 1 within the range of 100% to 0% TOF, and with values greater than one reflecting a proportionally increased block and/or concentration of NMB in the bloodstream beyond this level. Relaxation can be calculated by converting TOF measurements from percent to fractions and then subtracting from one:

$$\text{relaxation} = 1 - TOF/100\% \quad (6)$$

For example, a 10% TOF measurement is translated to a fraction of 0.1 and then to a 0.9 relaxation measurement. A TOF of 100% indicating full strength becomes a relaxation measurement of zero. Full relaxation in the TOF sense is represented by a TOF of zero, which is represented on the relaxation scale as a one. Saturated TOF values become greater than one in relaxation terms, e.g. a twitch count of two is 1.068 in relaxation units.

As another aspect, the relationship between T1/T0 and TOF can be mapped using a sigmoidal relationship. Sigmoidal relationships, being nonlinear, are more complicated than linear relationships such as Equation 5 but can better capture the dynamic of drug binding at the neuromuscular junction (NMJ) due to the general action of drugs at receptors as described by dose-response curves being sigmoidal in nature. The equation takes the form:

$$TOF = \frac{(T1/T0)^{\gamma}}{(T1/T0)^{\gamma} + E_{50}^{\gamma}} \quad (7)$$

where $\gamma$ is the Hill constant defining the rate of rise of the curve and $E_{50}$ is the T1/T0 response when TOF is 50%. In an iterative process, nonlinear estimation was used to determine the coeffcients of the equation. The datapoints used to construct Equation 5 can be used as fitting points. This can generate the relationship:

$$\text{response} = \frac{\text{free}^{3.8}}{\text{free}^{3.8} + 0.12^{3.8}} \quad (8)$$

The extrapolated TOF responses for the disappearance of the fourth, third, second and first twitch then become −1.3%, −5.7%, −22% and −35%, respectively.

With the relationship between the number of observable twitches and the level of relaxation established, control can be extended into the saturated region of TOF and the advantages of TOF can still be had. That is to say, mathematical algorithms can be used and linear controllers applied over a greater range of patient paralysis. Should deeper levels of paralysis be required this provides a method of delving deeper into saturation and will permit greater application of predictive control.

To encompass the nonlinearities into a linear model so that linear adaptive modeling techniques can be applied, a linear relationship of response and receptor occupancy was developed, called "pseudo-occupancy". Pseudo-occupancy is a linearized version of true receptor occupancy encompassing the delay to response and the saturation effects of the sensor, and is analogous to the drug concentration at the effector site (the NMJ for NMB drugs). This linearized model of occupancy includes levels greater than 100% (with a range of 0 to infinity) allowing for excessive doses larger than what is necessary to bind to all of the receptors, and accounting for the excess drug and how it is metabolized. Pseudo-occupancy can be considered a total of the multiples of the amount of drug required to bind all of the receptors present at the effector site. Some examples of pseudo-occupancy as compared to relaxation and comparable physiological representations are shown in Table 2.

TABLE 2

An approximate view of the relationship between NMB measurements, their physical manifestation and corresponding relaxation and occupancy measures.

| Measurement | Description | Relaxation | Pseudo-Occupancy |
|---|---|---|---|
| TOF = 100% | full strength | 0 | 0 |
| TOF = 30% | cannot hold head up | 0.7 | 0.77 |
| TOF = 0% | paralyzed | 1 | 0.88 |
| TOF = 1 twitch | paralyzed | 1.19 | 0.95 |
| TOF = 0 twitch | paralyzed | 1.312 | 1.0 |
| PTC < 7 | deep block | ≈1.5 | ≈1.1 |

Figure 2:
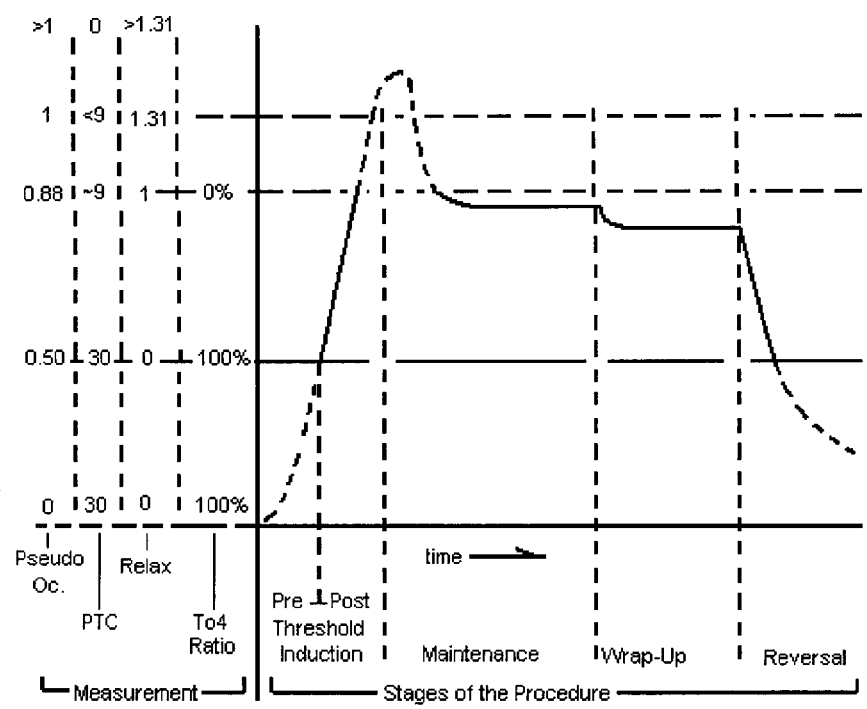
FIG. 2 illustrates levels of NMB drug and corresponding measurements through an exemplary procedure.

FIG. 2 shows how this could be in a typical case using NMB drugs. Prior to administration, measurements (PTC and TOF) are at full strength, there is no relaxation and no occupancy. In the induction pre-threshold phase, drug is administered and starts binding to receptors and pseudo-occupancy rises without any change in measurements or relaxation. Then the threshold is reached, and the post-threshold induction phase shows an increase in relaxation as well, while the measurements of contractility decrease. In this particular case the patient may be a high responder or intentionally overdosed, and saturation of the TOF measurement (when the measure of contractility is 0%) occurs. Relaxation at this point is greater than the maximum effect visible by the TOF, but there is still some contractility detectable by the PTC. This is the deep block phase. As the maintenance period continues, the drug is metabolized, pseudo-occupancy (and true occupancy) falls and response returns to the TOF measurement. A good level of paralysis is maintained throughout the rest of this period, then reduced and maintained in the wrap-up period, and finally allowed to come off completely in the reversal period. As the reversal period continues there is a return to full response as witnessed by the return of the TOF to 100%. Drug is still present and so pseudo-occupancy is still greater than zero, but decreasing.

Conversion of Standard Stimuli to TOF

The stimulation mode will change according to the patient's current and overall (for the whole case and maybe set by the anesthesiologist a priori) state of NMB, with the purpose of always having the best knowledge of the level of NMB for the patient. An example of this is shown in Table 3. The TOF is one sensing method at the start and through most of the case. It is used at induction and until the block becomes deep with partial TOF responses converted to eTOF measurements. Since this occurs prior to complete NMJ ACh receptor occupancy, there is still the possibility of some response. Response can be revealed by using a more ACh liberating method of stimulation such as PTC. If the deep block is unintended the PTC could be used to monitor and adapt the sensor while in saturation. If saturation is desired it might be necessary to solely use PTC. Once the drug has worn off to allow at least a partial TOF measurement, the measurement mode would switch back to TOF for the maintenance, wrap-up and reversal portions of the case.

Throughout this procedure, information gathered using non-TOF stimuli is converted into corresponding TOF data for modeling and control purposes. If the model was defined using a different stimulation mode, measurements could be converted to that mode.

TABLE 3

| Procedure stages and stimuli methods used (timewise not to scale). | |
|---|---|
| Induction ⇓ | TOF possibly with overstimulation and multiple sensors and compensation for greater frequency of use |
| Deepening block ⇓ | TOF with less than four measurable twitches, translated to TOF equiv. |
| Deep block (overshoot or by demand) ⇓ | PTC translated to TOF |
| Maintenance ⇓ | TOF |
| Wrap-up ⇓ | TOF |
| Reversal | TOF |

In one aspect of the methods, systems, devices, etc., herein, the ST measurement can be converted to a TOF measurement according to the relationship described above.

In another aspect of the methods, systems, devices, etc., herein, DBS measurements can be converted to TOF. A relationship between TOF and DBS measurements was found in [18], using the standard DBS consisting of two trains of three pulses at 50 Hz, spaced by 750 ms:

$$DBS = 1.07\ TOF - 3.2 \text{ or by rearranging} \tag{9}$$

$$TOF = \frac{DBS + 3.2}{1.07}$$

where DBS and TOF are both in percent units. Then, when DBS stimulation is indicated, the measurement is converted to TOF for use by the modeling and control algorithms.

In another aspect, PTC measurements can be converted to TOF. The PTC evokes response even when TOF and ST twitches cannot. The response evoked by the PTC indicates when the TOF will return. In [28], a correlation of PTC to time to return of the first twitch of the TOF when using rocuronium was found:

$$t = 18.8 - 6.46\sqrt{PTC} \tag{10}$$

where t is the number of minutes until return and PTC is the number of measurable post-tetanic twitches. For example, if a PTC of 1 is measured, the TOF will return in 12.34 minutes.

Based on Equation 10 the PTC will indicate the amount of time until a TOF is measurable. The amount of time can then be converted to timesteps and the model for occupancy can be used to arrive at what the present patient state is. Using a state space model (see any introductory Control Engineering textbook), drug flow through the patient can be described by the following equations:

$$X(t+1) = AX(t) + Bu(t) \tag{11}$$

$$y(t) = C(t)X(t) \tag{12}$$

where A is the state matrix, X is the patient state, y is an estimate of the amount of drug present at the NMJ and hence of the receptor occupancy, u is the drug input, and B and C are gains.

Assuming that the C matrix describing the patient is constant for the next N timesteps, then the current patient state can be calculated with the following equations:

$$X(t+N) = C(t)^{-1} y(t+N) = C(t)^T \frac{y(t+N)}{C(t)^T C(t)} \tag{13}$$

Assuming that there will be no inputs, from Equation 11:

$$X(t+1) = AX(t)$$

$$X(t+N) = A^N X(t) \tag{14}$$

and $$X(t) = A^{-N} X(t+N) \tag{15}$$

and the current pseudo-occupancy can be found by substitution into Equation 12:

$$y(t) = A^{-N} X(t+N) C(t) \tag{16}$$

In another embodiment of this aspect, if Equation 13 is not solvable the following method can be performed. The state matrix can be advanced into the future as at Equation 15. An estimate of y can be had:

$$y_{est}(t+N) = C(t)X(t+N) \tag{17}$$

Since the pseudo-occupancy system is linear, the ratio of y(t+N) to the y that should be seen when the TOF first begins to return (at full relaxation) will indicate the appropriateness of the model (the accuracy of A, B and C) and can be used to scale the X matrix:

$$X_{approx} = X(t+N) \frac{y_{est}(t+N)}{Oc} \tag{18}$$

where Oc is an estimate of the receptor occupancy (and thereby the amount of drug at the NMJ) when the TOF returns. This information can be used to construct an estimate of the current occupancy:

$$y(t) = C(t) X_{approx} \tag{19}$$

This can then be converted to an estimate of the corresponding TOF measurement.

Interconversion of Non-TOF Measurements

As the TOF measurement was judged to be the best of the commercially available modalities to this point, other modalities have been related back and interpreted as TOF alternatives. However, for various reasons, it might be required to use and work in terms of another, non-TOF modality.

In another embodiment, measurements are interconverted to accommodate the different measurement types, including translation of PTC to DBS as taught in [29]; and ST to PTC as mentioned in [30], and multiple conversions could be used to get from one type to another and back to the base type if needed. For example, DBS can be converted to TOF and from there to ST measurements.

Techniques, Systems, Etc. For Assessing NMB

The methods, systems, devices, etc., herein comprise techniques for assessing NMB and thereby increasing data and improving the quality of data already available.

To2 and To3 Measurements

Some error can be introduced as the relationship producing the extrapolated TOF values of Table 1 is not a continuous measurement, but is instead partially discrete. The measurement could be made more continuous by monitoring the change in T3 (the third twitch) and T2 (the second twitch) as they disappear.

In another aspect, To3 and To2 ("Train-of-3" and "Train-of-2") ratios of the magnitudes of the third and second twitch to the first twitch when administering the TOF stimulus are used and can then be translated to an alternative TOF measurement. Using data gathered from experiments the following exemplary correlations were found and can be used to interconvert partial-TOF measurements to corresponding TOF measurements:

$$TOF=1.07To2-23\%$$

$$TOF=0.97To3-3.4\% \tag{20}$$

By substitution into Equation 20, a To2 of zero produces an alternative TOF of −23% and a To3 of zero produces an alternative TOF of −3.4%. These values correspond well with the numbers provided for one and two twitches in Table 1, which are the scenarios that the zero value ratios represent.

The TOF typically provides more information through greater sensitivity and broader range of application, so the To3 and To2 may be preferable when only three and two twitches are evoked by the TOF. Their use provides a more continuous measurement without the discrete steps provided going from one twitch count to the next, reducing overall error.

The ACh Inventory Model

Figure 3:
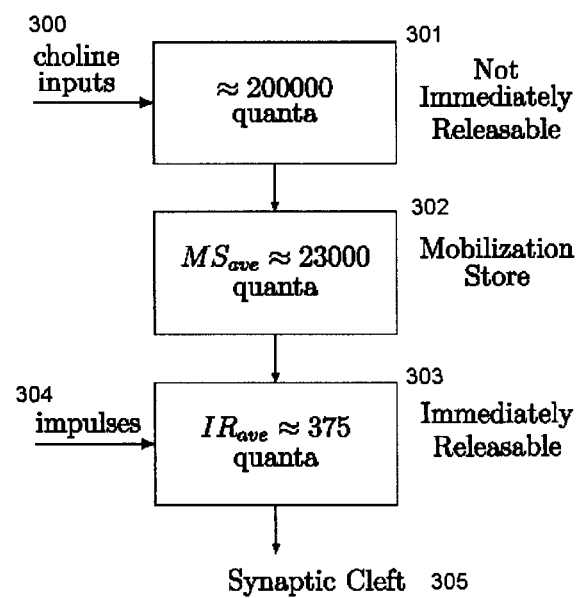
FIG. 3 illustrates a block diagram model of a quantal ACh model.

A description of the production, storage, mobilization and release of acetylcholine (ACh, the neurotransmitter at the NMJ) was presented for human intercostal muscle in [31]. The model compartmentalized the nerve terminal into tanks of not-immediately releasable, mobilizable and immediately releasable portions. The model is depicted in FIG. 3.

In the model, choline inputs 300 are received by the not-immediately-releasable tank 301 where they are reacted with acetyl amines to produce ACh and then stored in quantal vesicles. This is a large store typically containing about 200000 vesicles. It is considered to not deplete, provided drugs are not added to block the uptake of choline. Drugs blocking choline (e.g. hemicholinium) uptake are not used clinically. This tank provides ACh quanta to the mobilization store 302 at the rate of five quanta per input up to a maximum of 50 quanta per second. The mobilization store 302 is so named because its output to the immediately-releasable tank 303 is increased with demand and does so in a delayed fashion; demand "mobilizes" output. Its regular output is 0.14% per stimulation or 1.4% of the current store per second. This can be increased up to 2500 quanta per second at 70 Hz stimulation and then falls off. The size of the immediately releasable tank 303 is between 300 and 1000 quanta, with an average of 375 under normal circumstances. Electrical impulses 304 are received by the immediately releasable tank 303, causing release of ACh into synaptic cleft 305. This description was originally developed for the purpose of understanding NMJ physiology. Here the description has been made into a model (the "ACh model") to create data and insight for monitoring and control of NMB drugs in the form of a model of the neurotransmitter, ACh. The knowledge of the availability allows knowing what the capabilities of the muscle are and thereby the potential for muscle contraction.

In one embodiment, the ACh model can be used to maintain a model of ACh to know what to expect from any stimulation. This allows planning of the stimulation, reclassification of the patient if a prediction was judged incorrect, and interpretation of the measured response based on the circumstances of stimulation.

In another embodiment, the ACh model can be used to guide overstimulation—stimulation at rates higher than normal due to modification of the ACh output. Overstimulation can be used at the start of a procedure to quickly gather more data and better learn the patient's model to avoid over- and underdosing. For example, stimulation can be done using the TOF at once per 5 s instead of the usual once per 20 s. Over the long-term this results in depletion, however, in the short term more data is made available. The accuracy of patient modeling is improved by bringing forward twice as much data as would be had normally. Alternatively, overstimulation at double the normal frequency gathers double the data in the normal amount of time or the requisite data in half the time.

In another embodiment, this model can be used to estimate bias of results that came from running the stimulator at abnormally high rates, e.g. 5 s instead of 20 s between each TOF. This can support overstimulation (stimulation at greater rates than normally accepted due to reasons of long-term depletion) for brief periods of time to allow increased data collection when needed. In another embodiment, the ACh model supports an adaptive stimulator that modifies its stimuli pattern from standard patterns (e.g. TOF, DBS, ST and PTC) to produce an optimal stimulation. The ACh model can be used to predict what stimulations are viable and what causes distortion of the response given the current ACh stores. This allows use of the best stimulation modality for the circumstances (i.e. level of blockade), compromising between need for information (time constraints) and ability to release ACh (level of blockade constraints).

In another embodiment, the model can be used for classification of the patient as a high versus a low responder, by considering patient response as an indication of levels of ACh in their mobilizable stores. By noting how easily a depleted response can be obtained, the patient can be classified to a pre-existing patient subgroup or model.

In another embodiment, the ACh model can be used to predict when a return to normal function appears, if overstimulation produces a bias.

Modification of the Sensor

To facilitate the use of computer control of NMB as described herein, it may be useful to construct sensors and implement sensing methods more specific to the task.

In the background section, it was mentioned that different muscle types have different responses to NMB drugs. These differences can aid monitoring of the patient state, with the objectives of the monitoring dictating the muscle choice. For example, to prevent residual NMB a sensitive muscle with a slow recovery can be monitored, such as the adductor pollicis; and to reduce and/or avoid all movement a less sensitive muscle, such as the corrugator supercilii can be monitored. Based on the rating of the muscles found in Section 5.2 above, it may be best to have sensing at the corrugator supercilii during onset and deep block, and sensing at the adductor pollicis for reversability and recovery, with shared duties in periods of normal block.

In one embodiment these differences can be used to get more information on the patient state by measuring multiple muscles simultaneously. By stimulating and sensing at different muscle groups within the same case, the range of the usefulness of neuromuscular stimulation for monitoring of NMB can be extended. It may be possible to minimize dead time before response is typically seen by using the more sensitive muscle, and show longer onset and better resolution, and provide the greatest range of NMB information by using the less sensitive muscle. Measurement of response for both groups can be combined for analysis. This permits getting further data when one muscle group is already paralysed. This also permits fine control at the edge of deep blockade, control into deep blockade, reduction of saturation and situations of non-reversibility, and minimization of onset and deadtime.

Figure 4:
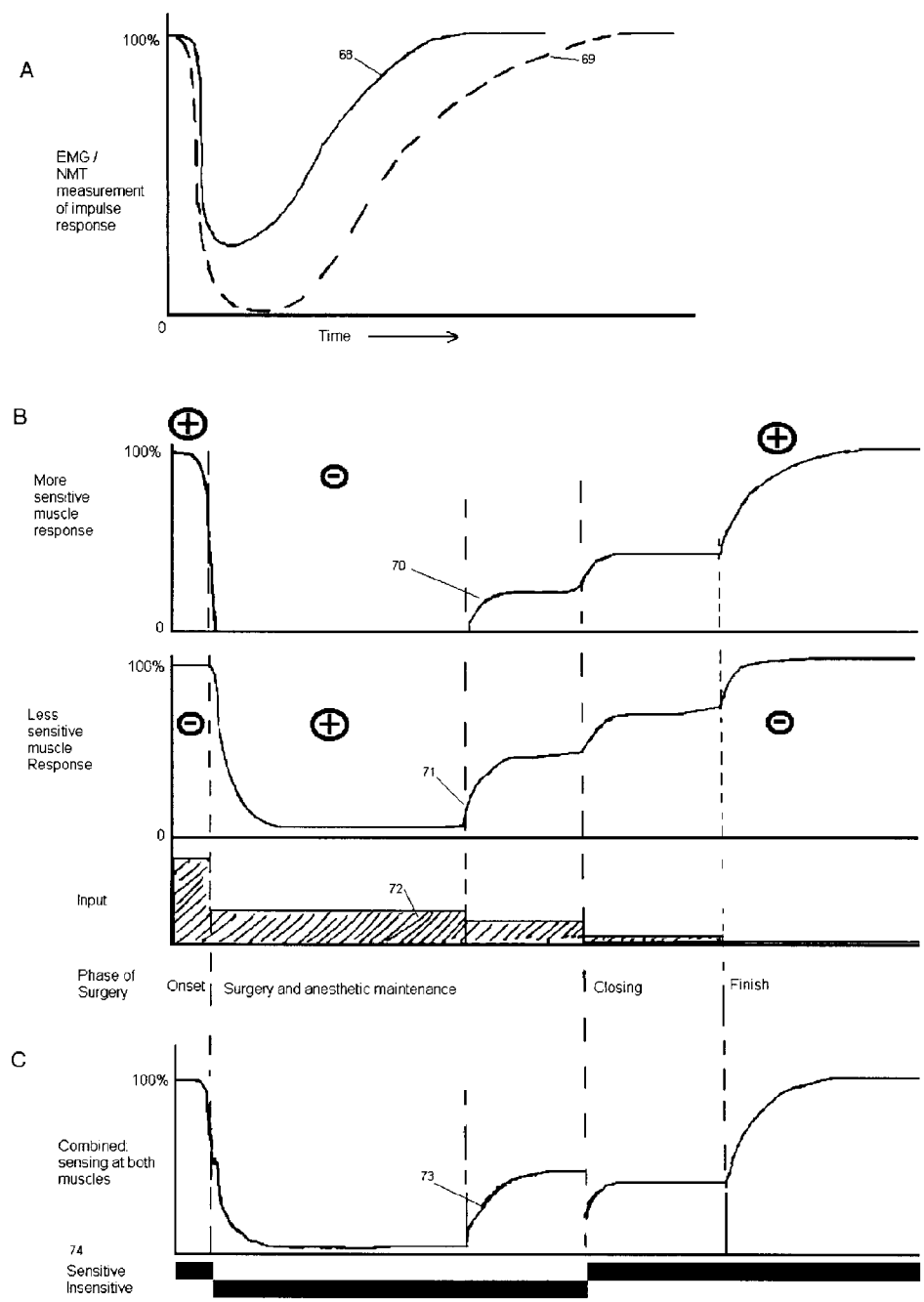
FIG. 4 illustrates sensing at different muscles throughout a procedure.

With paired (or more than two) muscles show different onset and recovery as the above do, stimulation and monitoring can be had at both muscles for the purpose of extending the range of sensing and control. Referring to FIG. 4, an example usage with two muscles of low impulse response 68 and high impulse response 69 is shown. The two muscles are exposed to the drug input defined by drug input trace 72, and react as less sensitive muscle response 71 and more sensitive muscle response 70. Sensing is alternated between the muscles as indicated by sensitive/insentive indicator 74 to take advantage of the muscles' optimal performance under the varied phases of surgery. The result is the combined sensing trace 73. In one embodiment, sensing is as follows: stimulation begins at the more sensitive group (e.g., adductor pollicis); as the patient is induced this muscle becomes saturated and sensing is halted at that muscle; sensing is started at the next most sensitive group (e.g. corrugator supercillii). Measurements can be translated into terms of the other muscle group; and sensing stops at the second group and switches back to the first more sensitive group once the first group recovers as judged with intermittent monitoring of the other group, continuous monitoring while in saturation or as according to a schedule based on modeling of the muscle's response to the drug and when it is predicted to return to function.

With more than two sensors, in the event of saturation of the monitored muscle, sensing can be moved to the next most sensitive group. Alternatively, sensing could continue at this group through saturation until recovery.

In another embodiment, inter-muscle translation of measurements can be done to produce corresponding muscle strengths between the two groups to provide information for modeling. This manifests as a translation to the particular group that the anesthesiologist wants to follow, or a switching back and forth between groups as the sensor moves between them to the group under control at the time, or a translation to the maximally sensitive group (as this will have the fuller range over time in terms of having any response. Similar to the eTOF measurement, this is an enhanced sensitive-muscle measure.

In one instantiation, stimulation of both muscle groups can be continuous throughout the procedure.

In another instantiation, stimulation can occur at the saturated muscle until it recovers.

In another instantiation, overlap of sensing between the two groups for a short period of time can occur. This may ensure a continuous and smooth switching between the groups and provide directly comparative data for translation of strengths between the groups.

In another instantiation, purpose driven stimulation can be used. As an example, muscle groups more representative of the laryngeal muscles can be stimulated at first to best judge intubation conditions. In another example, muscles more representative of the diaphragm could be monitored towards the end of the case to know when breathing will become spontaneous.

In another embodiment, the sensor can comprise one or more sets of stimulation leads and a corresponding number of transducers. The transducers can be comprised of EMG electrodes, accelerometers or otherwise.

Figure 7:
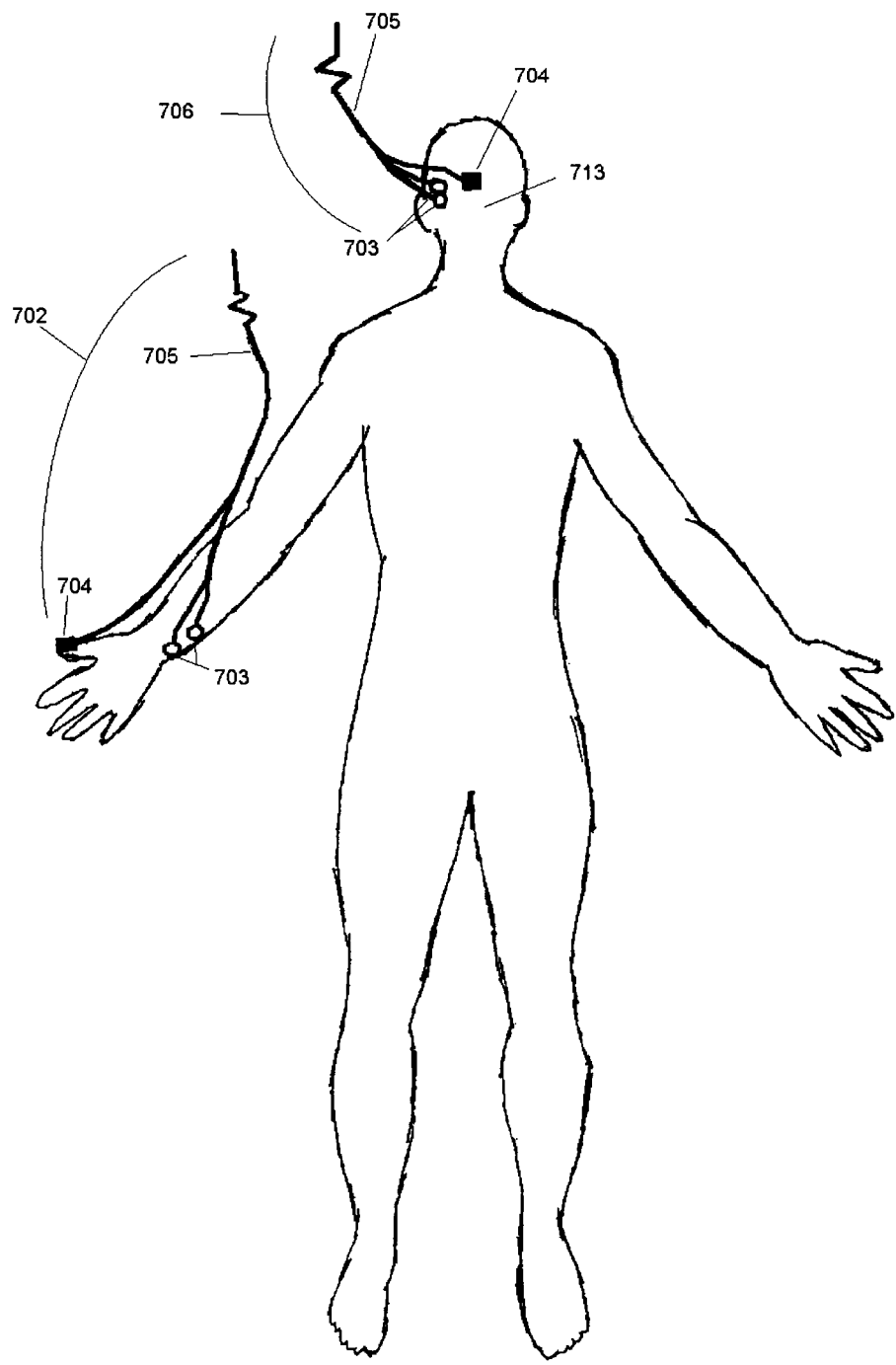
FIG. 7 illustrates a system using multiple sensors for increased range of measurement with sensors positioned at the adductor pollex and corrugator supercillii.

In another exemplary use, the sensors can be connected to different muscles to maximize range of stimulation, as in FIG. 7. Sensor 702 has been placed at the adductor pollicis of the right hand. Sensor 706 has been placed on the patient face 713 to stimulate muscles of the face. The sensors can include stimulating electrodes 703, transducing element 704 and connecting cables 705.

In another instantiation, the use of the sensors can be alternated to allow stimulation at a higher frequency than normally possible. Each sensor is operated at the normal stimulation rate (e.g. once per 20 s) but offset from one another by half the normal stimulation period. After combining the sensor measurements, this interdigitation in time increases the overall stimulation rate by a factor of two. This is useful for cases in which fine control of the level of blockade is required and thereby as much data as possible is required. Ophthalmic and neurological procedures may benefit from this. As the muscles may still have some differences between them and because the arrangement of the sensors may be different, there may be a need to adjust the response measured, particularly in amplitude.

Figure 6:
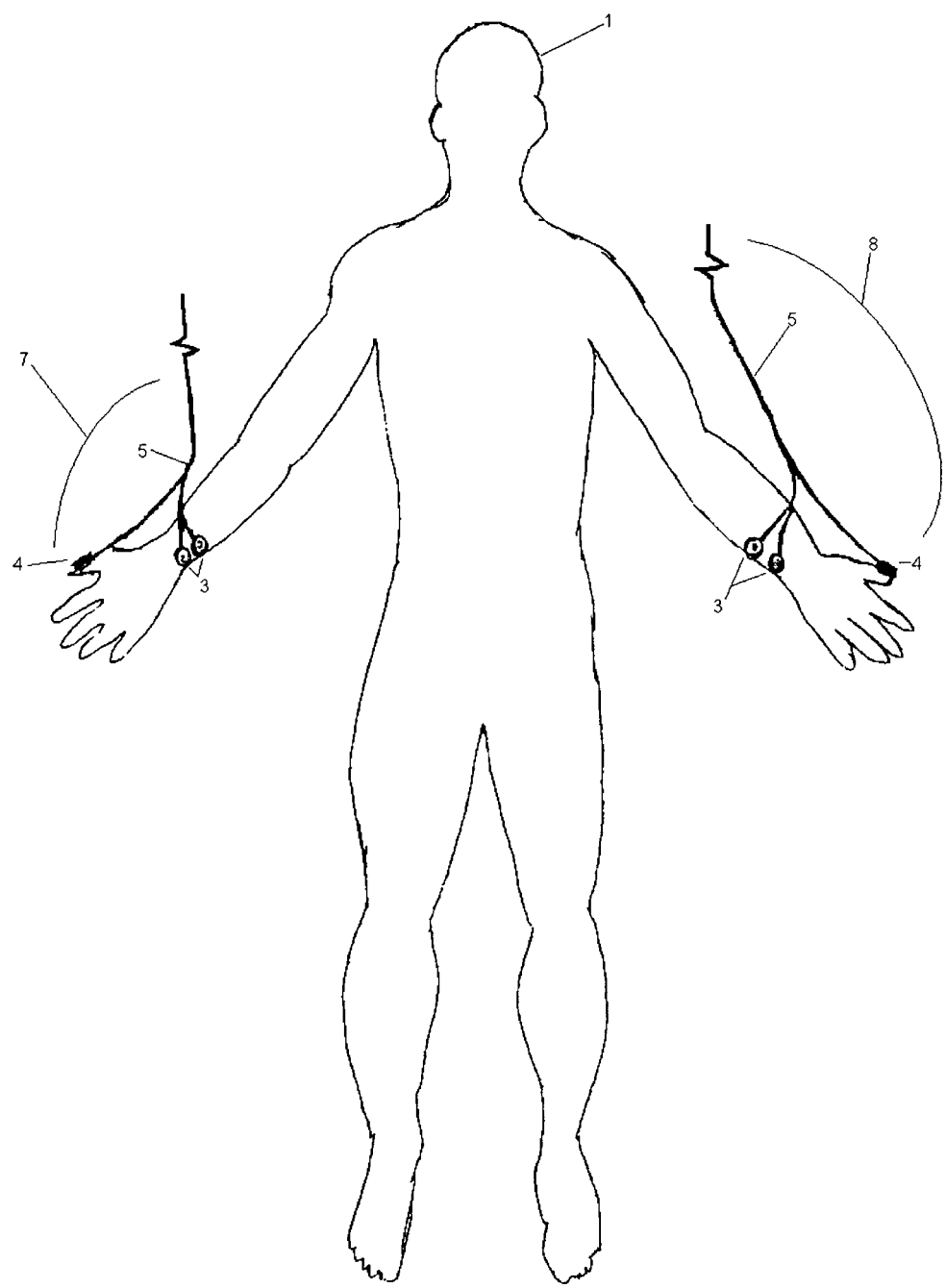
FIG. 6 illustrates a system using multiple sensors for increased frequency of data collection with sensors positioned on the adductor pollices.

As another exemplary use, the sensors are connected to similar muscles to increase data rate, as drawn in FIG. 6. The muscles being stimulated are the adductor pollices, using left muscle sensor 8 and right muscle sensor 7. Stimulating electrodes 3 are placed at the ulnar nerve and transducing element 4, in this case an accelerometer, is temporarily fixed to the patient 1 thumb. The sensors can connect to a monitor (not shown) through cable 5 to receive and transmit data and power.

Multiheaded Sensor

Figure 5:
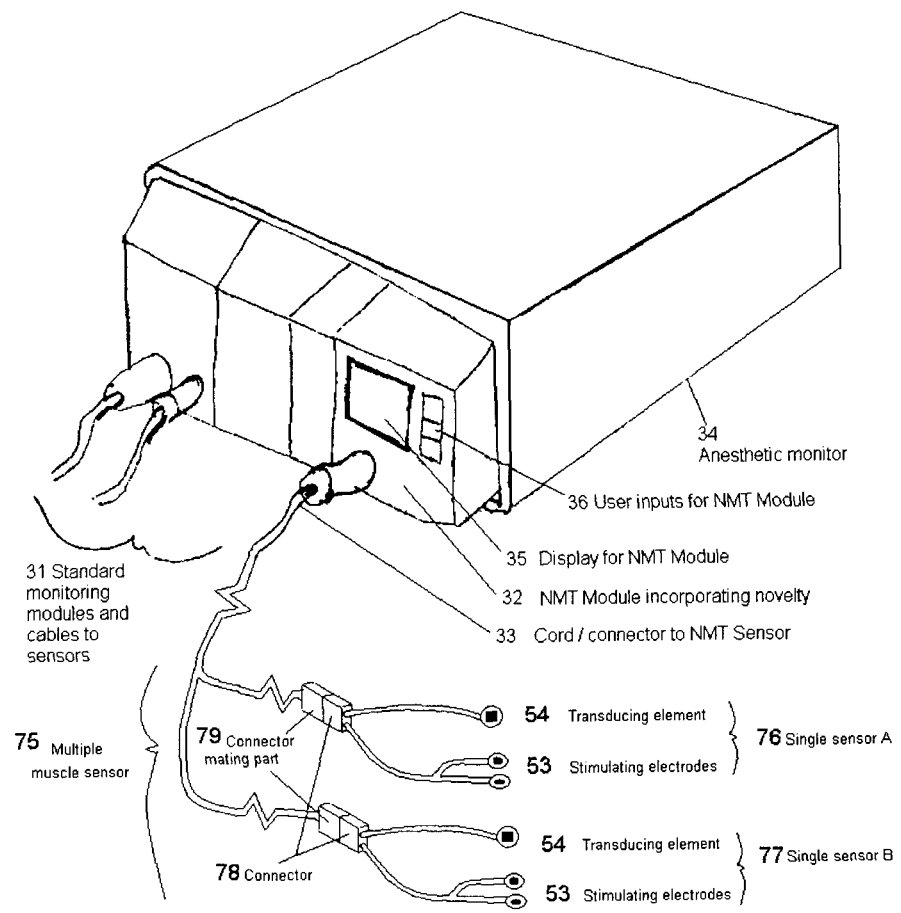
FIG. 5 illustrates the multiple muscle sensor as interfaced to a patient monitor.

An instantiation of a multiple muscle sensor is shown in FIG. 5 attached to a patient monitor, such as anesthesia monitor 34 with standard monitoring modules and cables 31. The algorithmic methods for improvement of NMB data collection can be incorporated into neuromuscular response measurement module 32 with appropriate electronics and software stored internally to itself, and insertable into anesthesia monitor 34. Data for indication of position of sensors and stimulation planning can be entered through a user interface 36 built into the NMT module 32 or another means. Output from the anesthesia monitor 34 regarding NMB data and data collection can be displayed on a screen 35 on the NMT module 32, on the anesthesia monitor's 34 screen or through a standalone unit.

The multiple muscle sensor 75 is comprised of cord and connector to NMT module 33, and two or more single muscle sensors 76 and 77, connected to cord and connector 33 through connector mating parts 79 and connectors 78. The single muscle sensors 76 and 77 are further comprised of connector 78, stimulating electrodes 53 and transducing element 54. Internal wiring (not shown) electrically connects the electrodes 53 and transducing element 54 to the connector 78, for providing stimulation output, sensing input and providing power, ground and other signals if needed. The multiple muscle sensor 75 has been drawn as comprised of the main section of cable joined to two separate sensors, 76 and 77, by the connector mating part 79. The connection allows for sensors 76 and 77 to be separately cleanable and/or disposable. In the case that multiple muscle sensor 75 was a single piece, connector mating parts 79 and connectors 78 would be eliminated, and electrodes and a mechanism of attaching transducer element 54 to the patient would be included.

Figure 8:
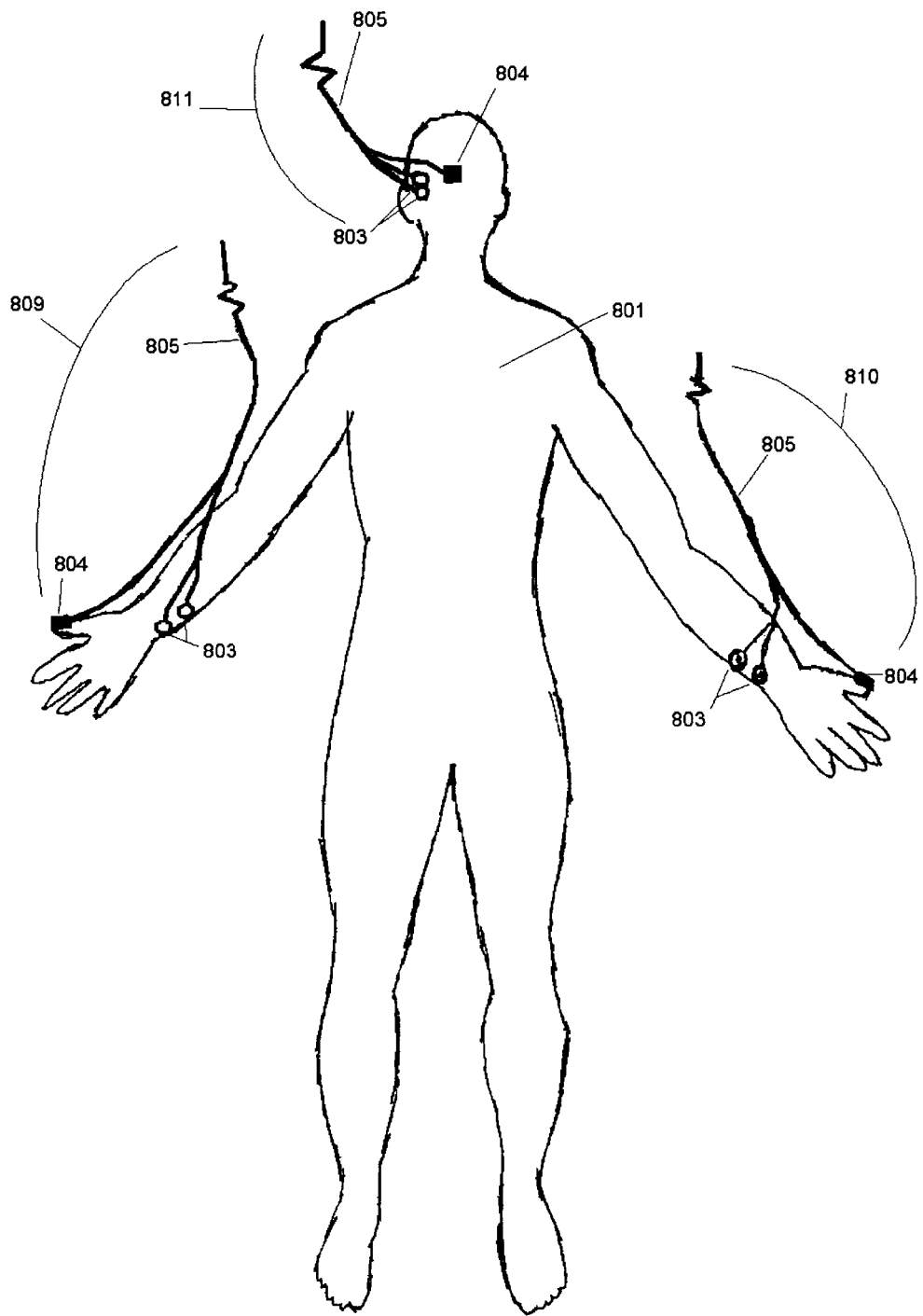
FIG. 8 illustrates a system using multiple sensors for both increased sensitivity and data collection with sensors positioned at both adductor pollices and one of the muscles of the face.

As another example, in FIG. 8 three sensors have been placed on the patient 801 to both increase data rate and to maximize range of stimulation. Sensor 809 has been placed at the first muscle of the increased data rate and more sensitive muscles. Sensor 810 has been placed at the second muscle of the increased data rate and more sensitive muscles. Sensor 811 has been placed at the relatively insensitive muscle for use of maximum range of stimulation. The sensors shown can be similar in construction to other sensors, including stimulating electrodes 803, transducing element 804 and connecting cables 805.

Devices to Facilitate Measurement

In this section, improved devices for the measurement of NMB are detailed. Devices are proposed to reduce user error and time to setup in the form of integrated sensor gloves and bandages. As well, a device is proposed to reduce electrical interference with measurements. Some of the improved devices may be made with handedness—to work on a left or a right side of the body specifically.

Sensor Glove

The effectiveness of the sensor typically depends upon electrode placement. As well, user acceptance of the sensor typically depends upon ease of use and setup time. A method of ensuring reliable placement and quick, easy use embeds the sensing and stimulation electrodes inside a glove for the patient to wear. This appears as the sensor glove 14 of FIG. 9. The sensor glove 14 is comprised of stimulating electrodes 903, transducing element 904, wires 16 either embedded into the material of the sensor glove 14 or taped to its top or bottom surface, and cable connection 905 to the controlling device.

Transducing element 904 has been drawn as an accelerometer. For other measurement techniques it can vary. For EMG testing, for instance, the accelerometer can be replaced by three or more electrodes.

Stimulating electrodes 903 and other electrodes, if used, could have means of improving electrical contact to the skin such as ultrasound gel, and means of improving fixation to the skin such as biocompatible adhesives placed beneath the electrodes. Sensor glove 14 could be made of stretchable material to allow for a one-size-fits-all. As with other gloves, however, sensor glove 14 can be made in different sizes to accommodate different users, e.g. sizes for small, medium and large hands; and e.g. average sizes for children, women and men. A complete glove (or sock or other) could interfere with surgical necessities such as the placement of intravenous lines and pulse oximetry sensors. Another embodiment of this device can have markings on the glove indicating areas that could be removed without damaging the utility of the glove for better access to the skin beneath. Markings can be made with printing processes including laser, ink, heat and pressure.

Figure 9:
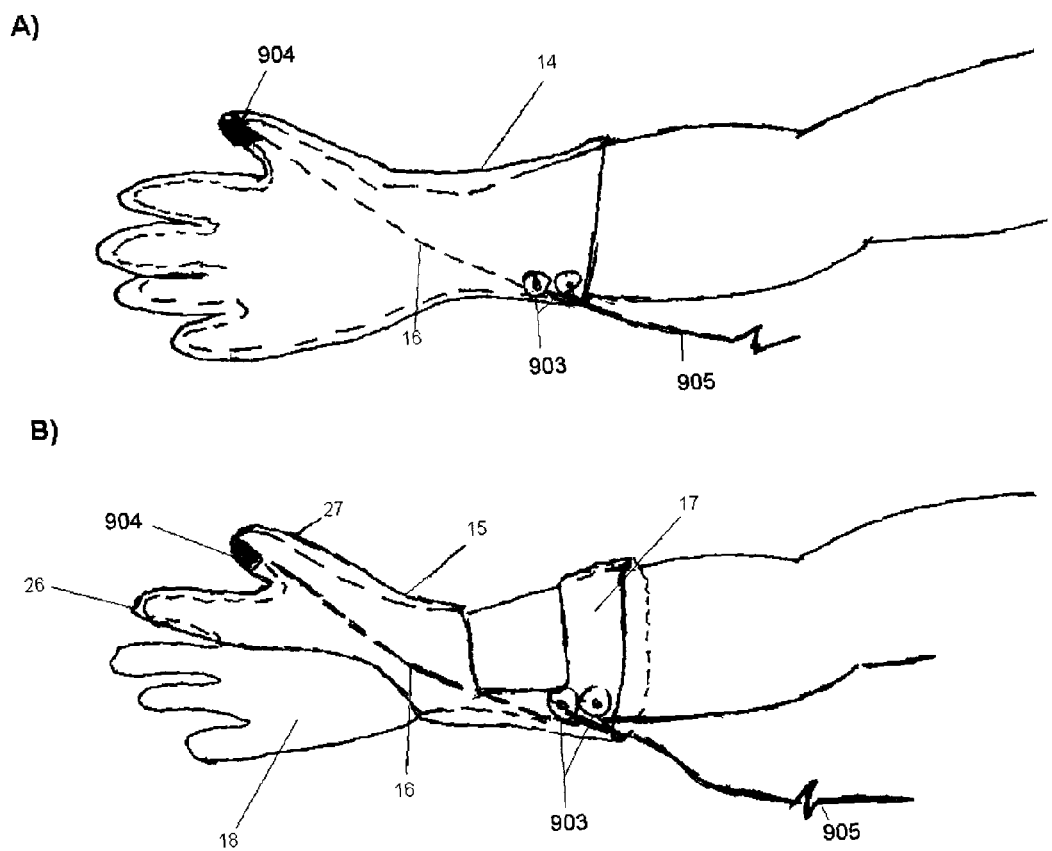
FIG. 9 illustrates different forms of a glove incorporating sensing for NMB, a general purpose version and another with portions removed to provide vein and skin access for intravenous/arterial lines and other sensors.

Another instantiation of this device is the skeleton glove 15 of the bottom drawing of FIG. 9. The skeleton glove 15 is a glove containing the stimulating electrodes 903, transducing element 904, wires 16 and cable connection 905 of the sensor glove 14 but with material not required having been removed. The glove material can comprise a thumb section 27 to hold the transducing element 904, an index finger section 26 to further stabilize the sensor and a band 17 to hold the stimulating electrodes 903 in place. Index finger section 26 can be optional in this design but could be required should sensing electrodes be desired at the flexor digiti minimi. Thumb section 27 can also be optional. This version of the sensor glove preserves the benefits of the methods, systems, devices, etc., herein while adding improved viewing of and access to the patient by exposing parts of the patient's hand 18. The design has been described for use with muscles of the hand. For other muscles the design would be modified to match the anatomy. For muscles of the face a mask or headband can be implemented. For muscles of the lower leg a sock or band form could be used.

Sensor Bandage

Figure 10:
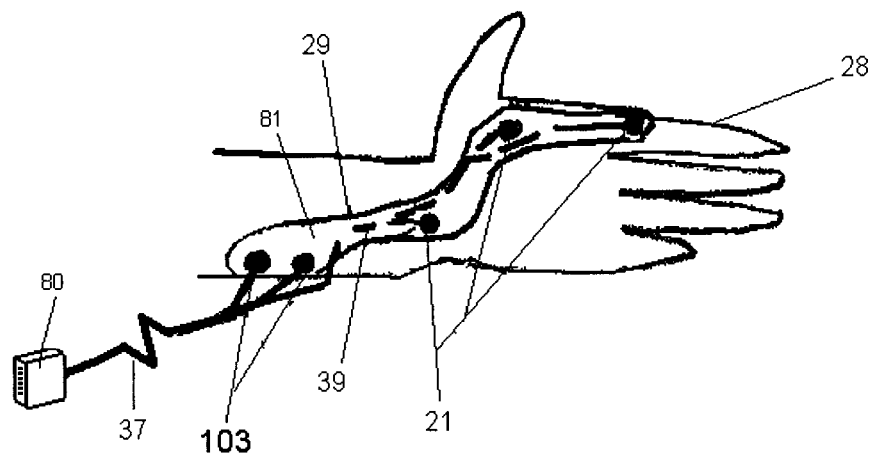
FIG. 10 illustrates different forms of a bandage incorporating sensing for NMB.
Figure 10:
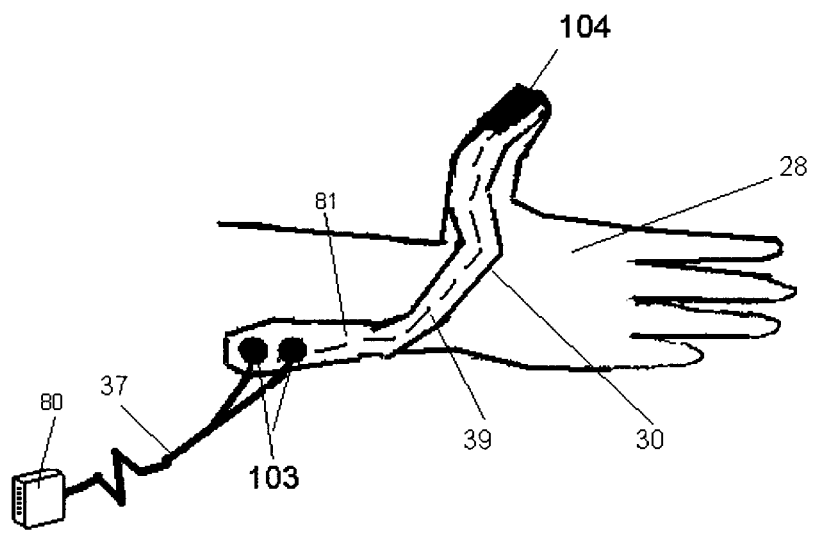

Versions of the sensor optimized for user acceptance are the EMG sensor bandage 29 and accelerometer bandage 30 of FIG. 10.

The version for use in EMG measurement can be comprised of stimulating electrodes 103, sensing electrodes 21, embedded wiring 39, external wiring 37 and connector 80. The electrodes of the bandage 29 and 30 can be similar to what is described in U.S. Pat. No. 3,590,810 Biomedical Body Electrode, in that they can have a conductive lead, electrolyte (conductive gel), body and adhesive annulus. The electrodes 103 and 21 are connected electrically to connector 80 through embedded wiring 39 and external wiring 37. Embedded wiring 39 and electrodes 103 and 21 are incorporated into or integrated with bandage material 81.

In another embodiment, the bandage has adhesive to hold the electrodes to the patient. The adhesive can be placed at the location of electrodes 103 and 21 or along the full length of bandage material 81. The bandage can have a liner backing to prevent loss of the electrolyte and to prevent accidental attachment when not desired. The liner and adhesive can be positioned only where required or can be run along the entire length of the bandage material 81. In one instantiation, bandage material 81 is made from a thin, flexible paper, plastic or other material and embedded wiring 39 and external wiring 37 are traces of conductive paint painted or conductive material glued onto bandage material 81. Connector 80 can be optional provided the connector mating part 79 is designed to receive bandage material 81. A sealant or a second layer of plastic could be applied to prevent electrical shorting of individual traces, but would have to leave exposed conductor at the endpoint for access by connector mating part 79.

In another instantiation, the device can be made for re-use and repeated sterilization. The connector 80, external wiring 37 and bandage material 81 are made from sterilization resistant materials. Electrodes 103 and 21 can be replaced by receptacles for connecting with separate electrodes, as the electrolyte and adhesive will degrade and/or be worn off with repeated sterilization.

Another instantiation of the sensor replaces sensing electrodes 21 with an accelerometer as transducing element 104. The accelerometer can be positioned at the tip of the thumb to capture maximum angular acceleration from the stimulation of the adductor pollicis. Similar constraints for materials, costs and sterilization would be applied to this design as to the first sensor bandage 29.

Shielding Overglove

Figure 11:
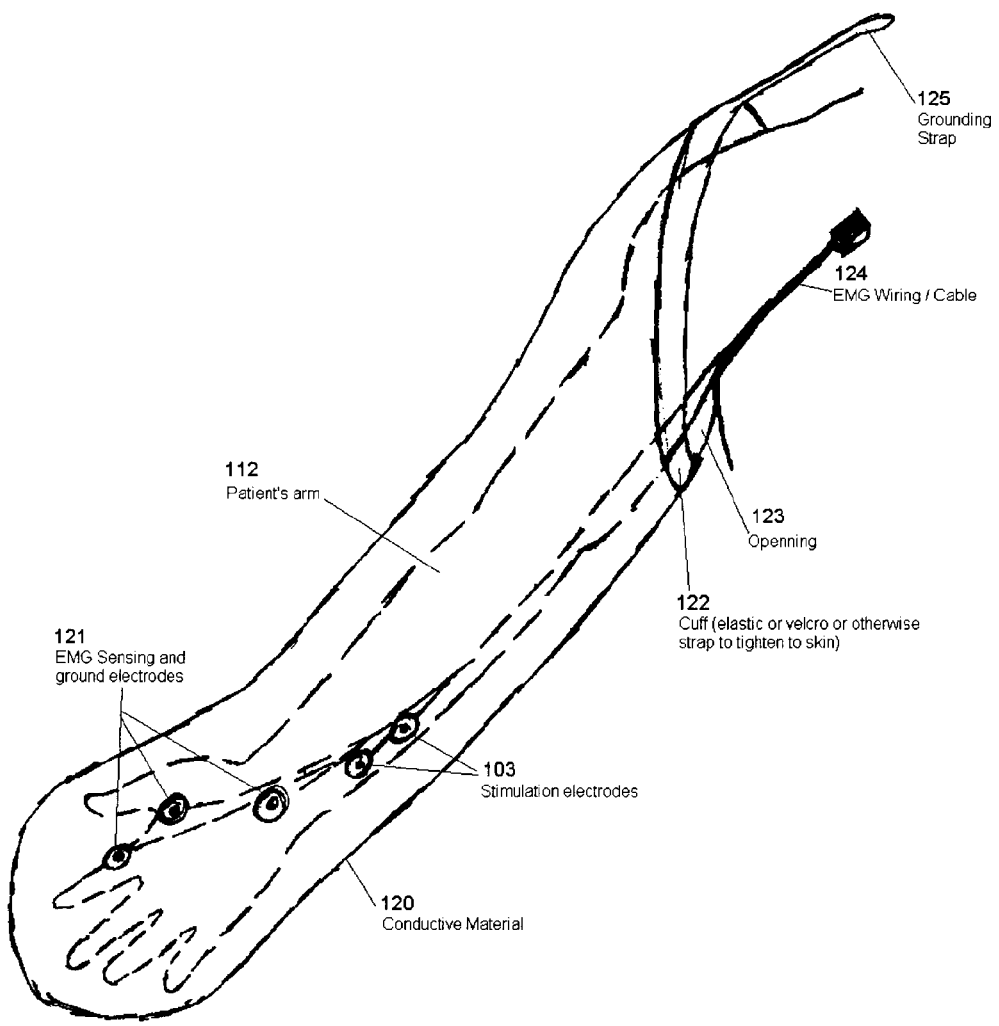
FIG. 11 illustrates a shielding bag to go over a NMB sensor for improvement of data collection by the NMB sensor.

Due to electrical noise from electric cauterizers and other devices, it is not uncommon for a sensor measurement, of neuromuscular response or otherwise, to be corrupted. The yield of data can be increased by shielding the sensor from radiated and surface electromagnetic interference. An aspect of the methods, systems, devices, etc., herein is a device that can do this, the shielding overglove, is shown in FIG. 11. In one embodiment this device is comprised of conductive material 120, grounding strap 125 and optional cuff 122. The conductive material 120 is cut and shaped to fit around the patient's arm 112 and the NMB sensor as represented by stimulation electrodes 113, EMG sensing electrodes 121 and EMG wiring 124.

The shielding overglove works in a similar fashion as a Farraday cage with radiated electromagnetic radiation and electric noise traveling on the surface of the patient being received by the conductive material 120 and grounded through grounding strap 125. The grounding strap 125 is connected to a suitable electric ground to remove the electromagnetic interference and prevent it from biasing the signal sensed by the sensor.

Exemplary materials that the conductive material 120 could be constructed from include conductive metal mesh, metal threads interweaved with fabric, metal-on-fabric, sputtered non-woven material such as polypropylene and metallic conductor mixes, and transparent or otherwise plastic or paper with painted on conductive inks. The conductive material 120 could be composed of one or more layers of the exemplary materials.

The cuff 122 holds the conductive material 120 in place and forms a light seal—that may or may not be contiguous—to the patient. Methods of implementation include a Velcro strap, an inflatable band, an elasticized band and adhesive. The cuff 122 is typically electrically conductive.

The shielding overglove is displayed for use on a hand and could also be designed for different appendages and muscles. As well, it could be made in different sizes to allow use by all patients, from neonates to adults. It may also be advantageous to make the conductive material 120 overly long to allow pulling the conductive material 120 up to the nearest joint and to cover as much of the patient as possible.

EXAMPLE IMPLEMENTATION: A Neuromuscular Blockade Advisory System (NMBAS) advises anesthesiologists on rocuronium dose magnitude and timing for maintenance of NMB at surgically favorable, yet easily reversible levels. A prospective randomized, controlled clinical trial was conducted to investigate the safety and effectiveness of an NMBAS that incorporated some of the methods and systems discussed in this application.

A prospective, randomized, controlled, clinical trial was conducted with n=73 patients (ASA physical status IIII) undergoing abdominal surgery under general anesthesia=1.5 h with neuromuscular blockade using rocuronium. Patients were allocated to standard care or NMBAS-guided rocuronium administration. The primary outcome variable was the incidence of intraoperative events reflecting inadequate NMB. Secondary outcome variables included TOF ratios at reversal and extubation; the total doses of rocuronium, reversal agents, anesthetics, and other drugs; the incidence of postoperative adverse events, and the incidence of anesthesiologist non-compliance with NMBAS recommendations.

Of 73 enrolled patients, n=30 per group were eligible for analysis. Patient demographics were comparable between the groups. The incidence in total intraoperative events associated with inadequate NMB was significantly lower in the NMBAS group compared to standard care (8/30 vs. 19/30; p<0.01). Mean TOF ratios prior to reversal were higher in the NMBAS group. Compared to standard practice, NMBAS-guided care was associated with improved NMB quality and higher TOF ratios at extubation, potentially reducing the risk of residual NMB and improving perioperative patient safety.

Terms

All terms used herein, are used in accordance with their ordinary meanings unless the context or definition clearly indicates otherwise. Also unless expressly indicated otherwise, the use of "or" includes "and" and vice-versa. Non-limiting terms are not to be construed as limiting unless expressly stated, or the context clearly indicates, otherwise (for example, "including", "having" and "comprising" typically indicate "including without limitation"). Singular forms, including in the claims, such as "a", "an" and "the" include the plural reference unless expressly stated, or the context clearly indicates, otherwise.

Unless stated specifically, patient refers to any biological system, human or other animal. While examples pertain more to human application, veterinary and experimental and other applications are included.

While the systems, methods, etc., herein have been described with specific reference to administration of NMB drugs, it is understood that the systems and methods taught herein can be applied to other drug therapies and other processes. Furthermore, the systems and methods taught herein can be applied beneficially to modeling and control (advisory and otherwise) of systems with non-negligible parameter variation.

From the foregoing, it will be appreciated that, although specific embodiments have been discussed herein for purposes of illustration, various modifications may be made without deviating from the scope of the discussion herein. Accordingly, the systems and methods, etc., include such modifications as well as all permutations and combinations of the subject matter set forth herein and are not limited except as by the appended claims or other claim having adequate support in the discussion herein.

What is claimed is:

1. A system for quantifying a neuromuscular response, the system comprising:
   (a) a stimulator configured to apply a first mode of stimulation to the patient, wherein the first mode of stimulation is Train Of Four (TOF);
   (b) one or more sensors configured to measure the patient's response to stimulation; and
   (c) a computer configured to:
      i. interpret the measured response to the first mode of stimulation as the measured response in terms of a second mode of stimulation when the measured response is not responsive to some or all of the stimulation from the first mode of stimulation, wherein the second mode of stimulation is one of Train of Three (TO3), Train of Two (TO2), and Single Twitch (ST); and
      ii. translate the measured response in terms of the second mode of stimulation into an output representative with respect to the first mode of stimulation with an equation.

2. The system of claim 1, wherein the computer is further configured to interpret the measured response to the first mode of stimulation as the measured response in terms of a second mode of stimulation when the measured response is responsive to three of the stimulations from the first mode of stimulation, wherein the second mode of stimulation is Train of Three (TO3); and the computer is further configured to translate the measured response in terms of the second mode of stimulation into an output representative with respect to the first mode of stimulation based on the equation:

$$TOF = 0.97 To3 - 3.4\%.$$

3. The system of claim 1, wherein the computer is further configured to interpret the measured response to the first mode of stimulation as the measured response in terms of a second mode of stimulation when the measured response is responsive to two of the stimulations from the first mode of stimulation, wherein the second mode of stimulation is Train of Two (TO2); and the computer is further configured to translate the measured response in terms of the second mode of stimulation into an output representative with respect to the first mode of stimulation based on the equation:

$$TOF = 1.07 To2 - 23\%.$$

4. The system of claim 1, wherein the computer is further configured to store a baseline Single Twitch measurement (T0), the computer is further configured to interpret the measured response to the first mode of stimulation as the measured response in terms of a second mode of stimulation, wherein the second mode of stimulation is Single Twitch (ST), and wherein the measured response of ST is defined as the ratio of the first responsive twitch (T1) to T0; and the computer is further configured to translate the measured response in terms of the second mode of stimulation into an output representative with respect to the first mode of stimulation based on the equation:

$$TOF=1.2*(T1/T0)-31\%.$$

5. The system of claim 1, wherein the computer is further configured to interpret the measured response to the first mode of stimulation as the measured response in terms of a second mode of stimulation, wherein the second mode of stimulation is Single Twitch (ST), wherein the measured response of ST is defined as the 25% when the measured response is responsive to three of the stimulations from the first mode of stimulation, wherein the measured response of ST is defined as 20% when the measured response is responsive to two of the stimulations from the first mode of stimulation, wherein the measured response of ST is defined as 10% when the measured response is responsive to one of the stimulations from the first mode of stimulation, wherein the measured response of ST is defined as 0% when there is no measured response to all of the stimulations from the first mode of stimulation, and wherein the measured response of ST is defined as the ratio (T1/T0); and the computer is further configured to translate the measured response in terms of the second mode of stimulation into an output representative with respect to the first mode of stimulation based on the equation:

$$TOF=1.2*(T1/T0)-31\%.$$

6. The system of claim 1, wherein the computer is further configured to advise a user of the patient's drug needs and/or the length of time until indicated response levels are reached.

7. The system of claim 1, wherein the computer is further configured to provide control for closed-loop drug administration.

8. A system for quantifying a neuromuscular response, the system comprising:
  (a) a stimulator configured to apply first and second modes of stimulation to the patient, wherein the first mode of stimulation is Train Of Four (TOF) and the second mode of stimulation is Post Tetanic Count (PTC);
  (b) one or more sensors configured to measure the patient's response to stimulation; and
  (c) a computer configured to:
    i. direct the stimulator to apply the second mode of stimulation when the measured response is not responsive to all of the stimulation from the first mode of stimulation; and
    ii. translate the measured response to the second mode of stimulation into an output representative with respect to the first mode of stimulation with an equation.

9. The system of claim 8, wherein the computer is further configured to advise a user of the patient's drug needs and/or the length of time until indicated response levels are reached.

10. The system of claim 8, wherein the computer is further configured to provide control for closed-loop drug administration.

11. A system for quantifying a neuromuscular response, the system comprising:
  (a) a stimulator configured to apply first and second modes of stimulation to the patient, wherein the first mode of stimulation is Train Of Four (TOF) and the second mode of stimulation is one of Double Burst Stimulation (DBS) or Single Twitch (ST);
  (b) one or more sensors configured to measure the patient's response to stimulation; and
  (c) a computer configured to:
    i. direct the stimulator to apply the first mode of stimulation;
    ii. direct the stimulator to apply the second mode of stimulation; and
    iii. translate the measured response to the second mode of stimulation into an output representative with respect to the first mode of stimulation with an equation.

12. The system of claim 11, wherein the computer is further configured to translate the measured response to the second mode of stimulation into an output representative with respect to the first mode of stimulation based on the equation:

$$TOF=(DBS+3.2\%)/1.07$$

when the second mode of stimulation is DBS.

13. The system of claim 11, wherein the computer is further configured to store a baseline Single Twitch measurement (T0), the computer is further configured to interpret the measured response to the first mode of stimulation as the measured response in terms of a second mode of stimulation, wherein the second mode of stimulation is Single Twitch (ST), and wherein the measured response of ST is defined as the ratio of the first responsive twitch (T1) to T0; and the computer is further configured to translate the measured response in terms of the second mode of stimulation into an output representative with respect to the first mode of stimulation based on the equation:

$$TOF=1.2*(T1/T0)-31\%.$$

14. The system of claim 11, wherein the computer is further configured to advise a user of the patient's drug needs and/or the length of time until indicated response levels are reached.

15. The system of claim 11, wherein the computer is further configured to provide control for closed-loop drug administration.

16. A system for quantifying a neuromuscular response, the system comprising:
  (a) a stimulator configured to apply first and second modes of stimulation to the patient, wherein the first mode of stimulation is Double Burst Stimulation (DBS) and the second mode of stimulation is Train Of Four (TOF);
  (b) one or more sensors configured to measure the patient's response to stimulation; and
  (c) a computer configured to:
    i. direct the stimulator to apply the first mode of stimulation;
    ii. direct the stimulator to apply the second mode of stimulation; and
    iii. translate the measured response to the second mode of stimulation into an output representative with respect to the first mode of stimulation with an equation.

17. The system of claim 16, wherein the computer is further configured to translate the measured response to the second mode of stimulation into an output representative with respect to the first mode of stimulation based on the equation:

$$DBS=1.07TOF-3.2\%.$$

18. The system of claim 16, wherein the computer is further configured to advise a user of the patient's drug needs and/or the length of time until indicated response levels are reached.

19. The system of claim 16, wherein the computer is further configured to provide control for closed-loop drug administration.

20. A system for quantifying a neuromuscular response, the system comprising:
  (a) a stimulator configured to apply first and second modes of stimulation to the patient, wherein the first mode of stimulation is Single Twitch (ST) and the second mode of stimulation is Train Of Four (TOF);
(b) one or more sensors configured to measure the patient's response to stimulation; and
(c) a computer configured to:
  i. direct the stimulator to apply the first mode of stimulation;
  ii. direct the stimulator to apply the second mode of stimulation; and
  iii. translate the measured response to the second mode of stimulation into an output representative with respect to the first mode of stimulation with an equation.

21. The system of claim 20, wherein the computer is further configured to store a baseline Single Twitch measurement (T0) and wherein the measured response of ST is defined as the ratio of the first responsive twitch (T1) to T0; and the computer is further configured to translate the measured response in terms of the second mode of stimulation into an output representative with respect to the first mode of stimulation based on the equation:

$$(T1/T0) = TOF/1.2 + 31\%.$$

22. The system of claim 20, wherein the computer is further configured to advise a user of the patient's drug needs and/or the length of time until indicated response levels are reached.

23. The system of claim 20, wherein the computer is further configured to provide control for closed-loop drug administration.

24. A method for controlling the administration of a neuromuscular blockade based on a patient's neuromuscular response, the method comprising:
(a) applying a first mode of stimulation to the patient, wherein the first mode of stimulation is Train Of Four (TOF);
(b) measuring the response produced by the first mode of stimulation;
(c) interpreting the measured response to the first mode of stimulation as the measured response in terms of a second mode of stimulation when the measured response is not responsive to some of the stimulation from the first mode of stimulation, wherein the second mode of stimulation is one of Train of Three (TO3), Train of Two (TO2), and Single Twitch (ST);
(d) translating the measured response in terms of the second mode of stimulation into an output representative with respect to the first mode of stimulation with an equation; and
(e) controlling the administration of the neuromuscular blockade via computer based on the measured response when the patient is responsive to all of the stimulation from the first mode of stimulation, and controlling the administration of the neuromuscular blockade based on the output representative with respect to the first mode of stimulation when the patient is not responsive to some or all of the stimulation from the first mode of stimulation.

* * * * *